US012727769B2

(12) United States Patent
Hui et al.

(10) Patent No.: US 12,727,769 B2
(45) Date of Patent: Sep. 8, 2026

(54) NEAR-FIELD COHERENT SENSING METHODS AND SYSTEMS

(71) Applicant: Cornell University, Ithaca, NY (US)

(72) Inventors: Xiaonan Hui, Ithaca, NY (US); Edwin C. Kan, Ithaca, NY (US)

(73) Assignee: Cornell University, Ithaca, NY (US)

( * ) Notice: Subject to any disclaimer, the term of this patent is extended or adjusted under 35 U.S.C. 154(b) by 1225 days.

(21) Appl. No.: 17/598,180

(22) PCT Filed: Mar. 26, 2020

(86) PCT No.: PCT/US2020/025085
§ 371 (c)(1),
(2) Date: Sep. 24, 2021

(87) PCT Pub. No.: WO2020/198544
PCT Pub. Date: Oct. 1, 2020

(65) Prior Publication Data

US 2022/0175254 A1 Jun. 9, 2022

Related U.S. Application Data

(60) Provisional application No. 62/955,994, filed on Dec. 31, 2019, provisional application No. 62/824,261,
(Continued)

(51) Int. Cl.
*A61B 5/0205* (2006.01)
*A61B 5/024* (2006.01)
(Continued)

(52) U.S. Cl.
CPC ........ *A61B 5/0205* (2013.01); *A61B 5/02405* (2013.01); *A61B 5/0265* (2013.01); *H04B 5/73* (2024.01); *H04W 4/38* (2018.02)

(58) Field of Classification Search
CPC .......... A61B 5/00-7495; A61B 5/0205; A61B 5/02405; A61B 5/0265; A61B 5/6891;
(Continued)

(56) References Cited

U.S. PATENT DOCUMENTS 4,958,638 A * 9/1990 Sharpe ................. A61B 5/0507
600/407
5,640,683 A 6/1997 Gifford et al.
(Continued)

FOREIGN PATENT DOCUMENTS

EP 0853392 A2 7/1998
EP 0670558 B1 5/2000
(Continued)

OTHER PUBLICATIONS

Hui, X. and Kan, E.C., Monitoring vital signs over multiplexed radio by near-field coherent sensing, Nature Electronics, Nov. 27, 2017, vol. 1, pp. 74-78. Nov. 27, 2017.
(Continued)

*Primary Examiner* — Tse W Chen
*Assistant Examiner* — Evelyn Grace Park
(74) *Attorney, Agent, or Firm* — Barnes & Thornburg

(57) ABSTRACT

Near-field coherent sensing (NCS) methods and systems are described herein. The techniques may be used to monitor vital signs is introduced herein. Multiple-input, multiple output near-field techniques may be used to characterize motion. In some embodiments, the methods and systems are used to measure cardiac motion. In some embodiments, the disclosed system is integrated into a seat, such as, for example, a car seat. The system be configured to monitor the vital signs of a seat occupant with multiple sensing points. The sensor can be integrated into the cushion and hence "invisible" to the user.

20 Claims, 27 Drawing Sheets

Related U.S. Application Data filed on Mar. 26, 2019, provisional application No. 62/824,268, filed on Mar. 26, 2019.

(51) Int. Cl.

| | |
|---|---|
| ***A61B 5/0265*** | (2006.01) |
| ***H04B 5/73*** | (2024.01) |
| ***H04W 4/38*** | (2018.01) |

(58) Field of Classification Search

CPC . H04B 5/73; H04W 4/38; G01S 7/415; G01S 13/88; G01S 13/585; G01S 7/41–418; G06K 7/10336

See application file for complete search history.

(56) References Cited

U.S. PATENT DOCUMENTS

| | | | | |
|---|---|---|---|---|
| 5,777,561 | A | 7/1998 | Chieu et al. | |
| 5,873,025 | A | 2/1999 | Gifford et al. | |
| 5,935,077 | A | 8/1999 | Ogle | |
| 5,952,922 | A | 9/1999 | Shober | |
| 6,650,230 | B1 | 11/2003 | Gifford et al. | |
| 7,096,133 | B1 | 8/2006 | Martin et al. | |
| 7,603,894 | B2 | 10/2009 | Breed | |
| 7,693,626 | B2 | 4/2010 | Breed et al. | |
| 7,938,013 | B2 | 5/2011 | Hughes et al. | |
| 8,024,084 | B2 | 9/2011 | Breed | |
| 8,267,325 | B2 | 9/2012 | Phaneuf | |
| 8,721,559 | B2 | 5/2014 | Peterson et al. | |
| 8,725,311 | B1 * | 5/2014 | Breed | A61B 5/11 701/1 |
| 8,989,867 | B2 | 3/2015 | Chow et al. | |
| 9,330,561 | B2 | 5/2016 | Proud | |
| 9,443,358 | B2 | 9/2016 | Breed | |
| 9,489,813 | B1 | 11/2016 | Beigel | |
| 9,645,234 | B2 | 5/2017 | Khan et al. | |
| 9,744,369 | B2 | 8/2017 | Poon et al. | |
| 9,949,691 | B2 | 4/2018 | Huppert et al. | |
| 10,863,313 | B2 | 12/2020 | Markhovsky et al. | |
| 2003/0139691 | A1 | 7/2003 | Kumar et al. | |
| 2004/0032363 | A1 | 2/2004 | Schantz et al. | |
| 2005/0190098 | A1 | 9/2005 | Bridgelall et al. | |
| 2005/0206555 | A1 | 9/2005 | Bridgelall et al. | |
| 2006/0012476 | A1 | 1/2006 | Markhovsky | |
| 2006/0022800 | A1 | 2/2006 | Krishna et al. | |
| 2006/0224048 | A1 | 10/2006 | Devaul et al. | |
| 2006/0284727 | A1 | 12/2006 | Steinke | |
| 2007/0222560 | A1 | 9/2007 | Posamentier | |
| 2007/0279194 | A1 | 12/2007 | Carrender et al. | |
| 2008/0030244 | A1 | 2/2008 | Leifso | |
| 2008/0299933 | A1 | 12/2008 | Chang et al. | |
| 2009/0167699 | A1 | 7/2009 | Rosenblatt et al. | |
| 2010/0039228 | A1 | 2/2010 | Sadr et al. | |
| 2010/0060424 | A1 | 3/2010 | Wild et al. | |
| 2010/0201492 | A1 | 8/2010 | Koo et al. | |
| 2010/0214065 | A1 | 8/2010 | Maltseff et al. | |
| 2010/0292568 | A1 | 11/2010 | Droitcour et al. | |
| 2011/0028854 | A1 | 2/2011 | Addison et al. | |
| 2011/0148710 | A1 | 6/2011 | Smid et al. | |
| 2011/0187600 | A1 | 8/2011 | Landt | |
| 2012/0235689 | A1 | 9/2012 | Jau et al. | |
| 2012/0235856 | A1 | 9/2012 | Nogami et al. | |
| 2012/0249302 | A1 | 10/2012 | Szu | |
| 2012/0256730 | A1 | 10/2012 | Scott et al. | |
| 2013/0030257 | A1 * | 1/2013 | Nakata | G01S 13/87 600/407 |
| 2013/0030259 | A1 | 1/2013 | Thomsen et al. | |
| 2013/0043981 | A1 | 2/2013 | Wang et al. | |
| 2013/0165770 | A1 | 6/2013 | Li et al. | |
| 2013/0289379 | A1 | 10/2013 | Song et al. | |
| 2014/0292491 | A1 | 10/2014 | Maltseff et al. | |
| 2014/0330540 | A1 | 11/2014 | Lin et al. | |
| 2015/0198708 | A1 | 7/2015 | Khan et al. | |
| 2015/0282711 | A1 | 10/2015 | Thomas et al. | |
| 2016/0143557 | A1 | 5/2016 | Kahlman et al. | |
| 2016/0166160 | A1 | 6/2016 | Casale | |
| 2016/0338798 | A1 | 11/2016 | Vora et al. | |
| 2017/0055872 | A1 | 3/2017 | Tupin, Jr. | |
| 2017/0065184 | A1 | 3/2017 | Barak | |
| 2017/0082741 | A1 * | 3/2017 | Adib | G01S 13/726 |
| 2017/0108452 | A1 | 4/2017 | Carlson | |
| 2017/0367619 | A1 | 12/2017 | Zhan | |
| 2018/0032768 | A1 | 2/2018 | Ganesan et al. | |
| 2019/0261137 | A1 | 8/2019 | Markhovsky et al. | |
| 2020/0022607 | A1 * | 1/2020 | Pratt | A61B 5/0803 |
| 2020/0170514 | A1 | 6/2020 | Hui et al. | |
| 2020/0236545 | A1 * | 7/2020 | Xu | A61B 5/1135 |

FOREIGN PATENT DOCUMENTS

| | | | |
|---|---|---|---|
| EP | 1744267 | A2 | 1/2007 |
| WO | 2016065368 | A1 | 4/2016 |
| WO | 2017093391 | A1 | 6/2017 |
| WO | 2017153907 | A1 | 9/2017 |
| WO | 2018011697 | A1 | 1/2018 |
| WO | 2018/232414 | A1 | 12/2018 |

OTHER PUBLICATIONS

Saccone, L., Near-Field Coherent Sensing Used to Monitor Vital Signs, Engineering News, Nov. 30, 2017, 4 pages. Nov. 30, 2017.

* cited by examiner

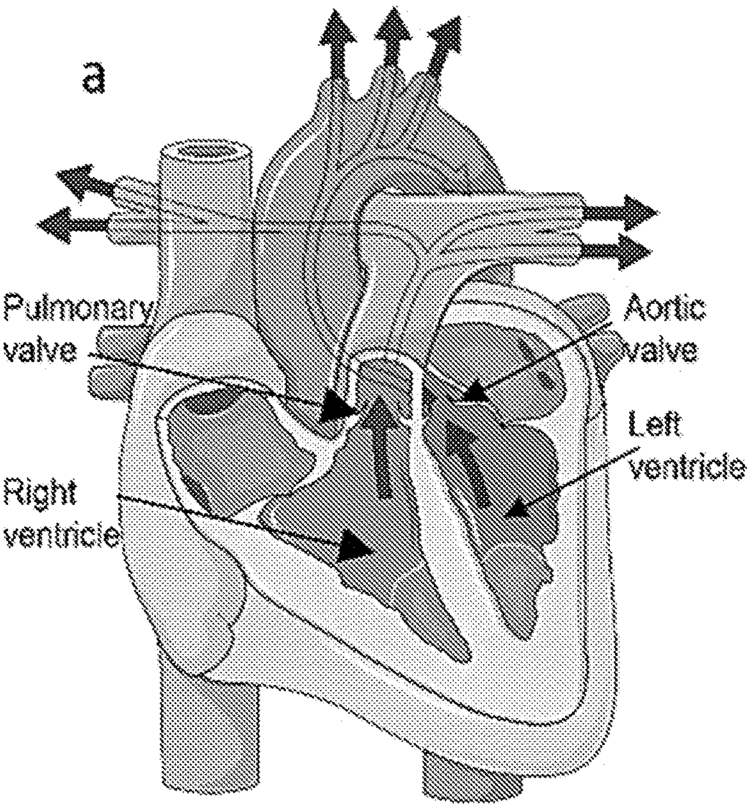
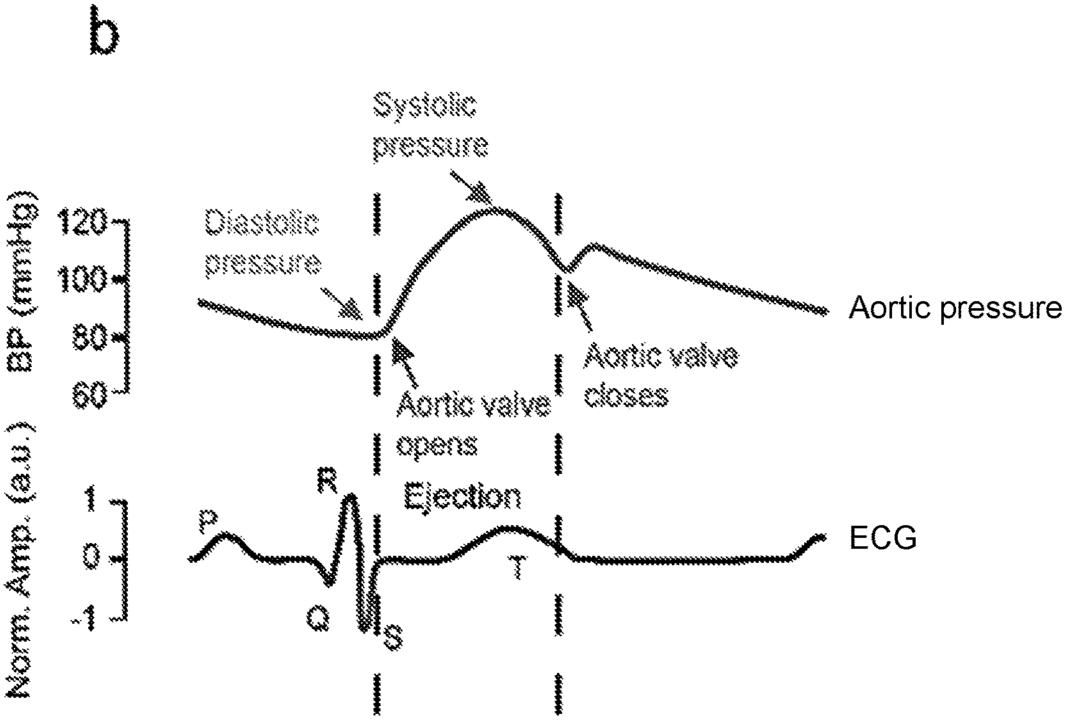
Fig. 6 (a-b)

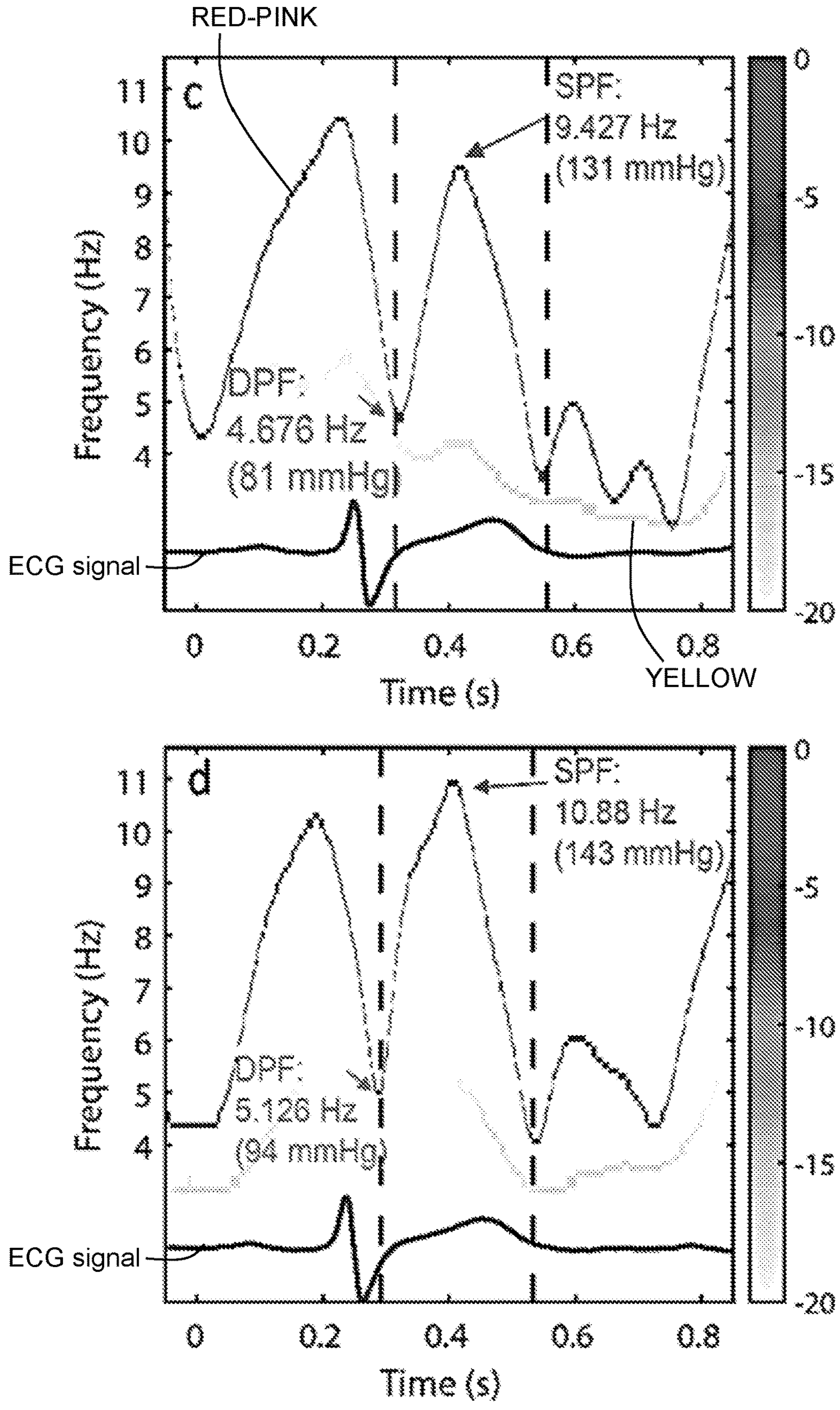
Fig. 6 (c-d)

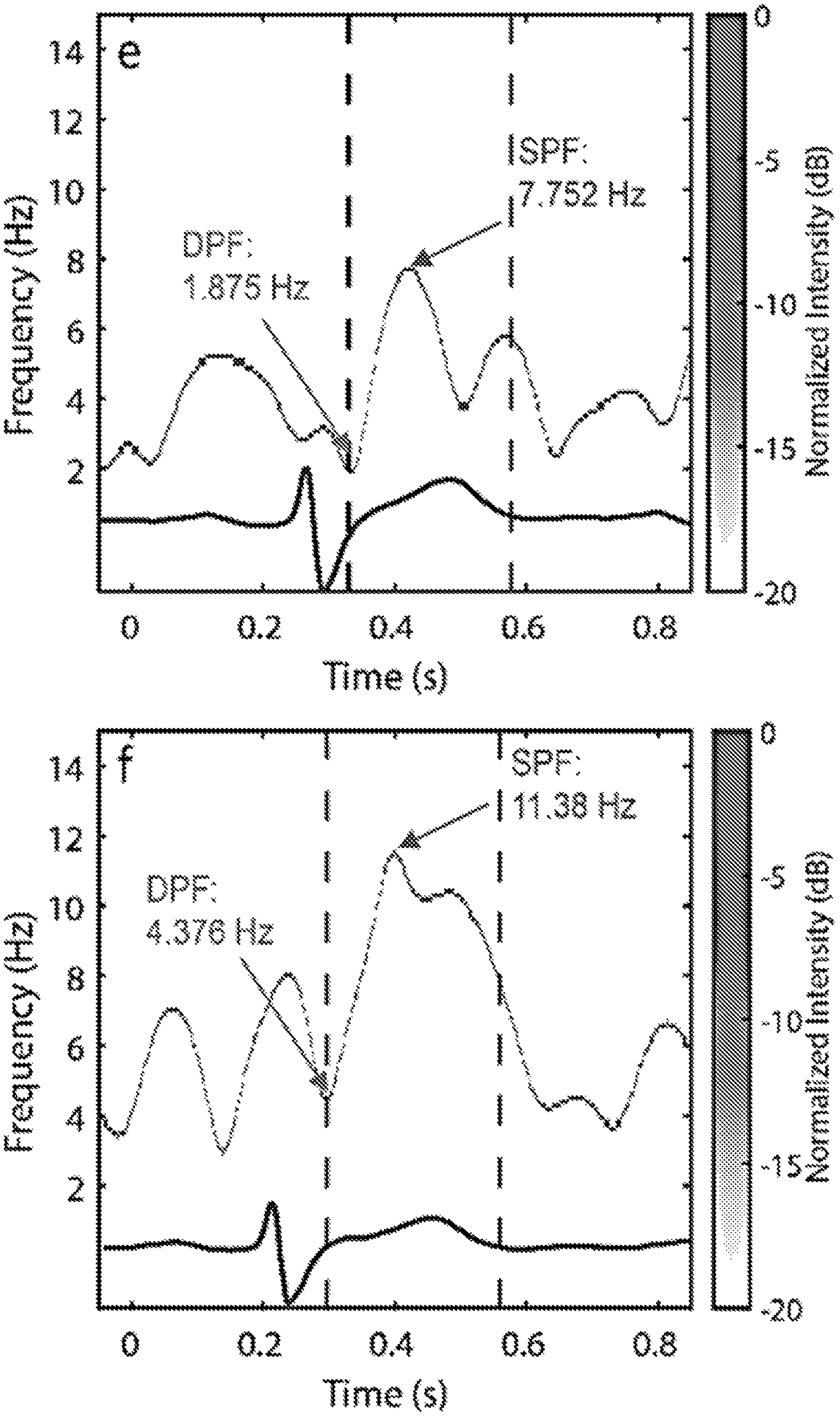
Fig. 6 (e-f)

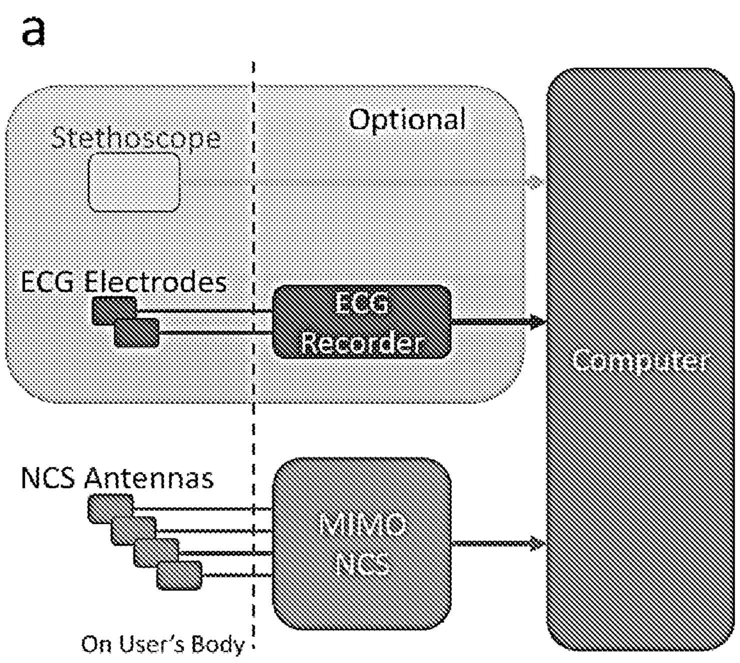
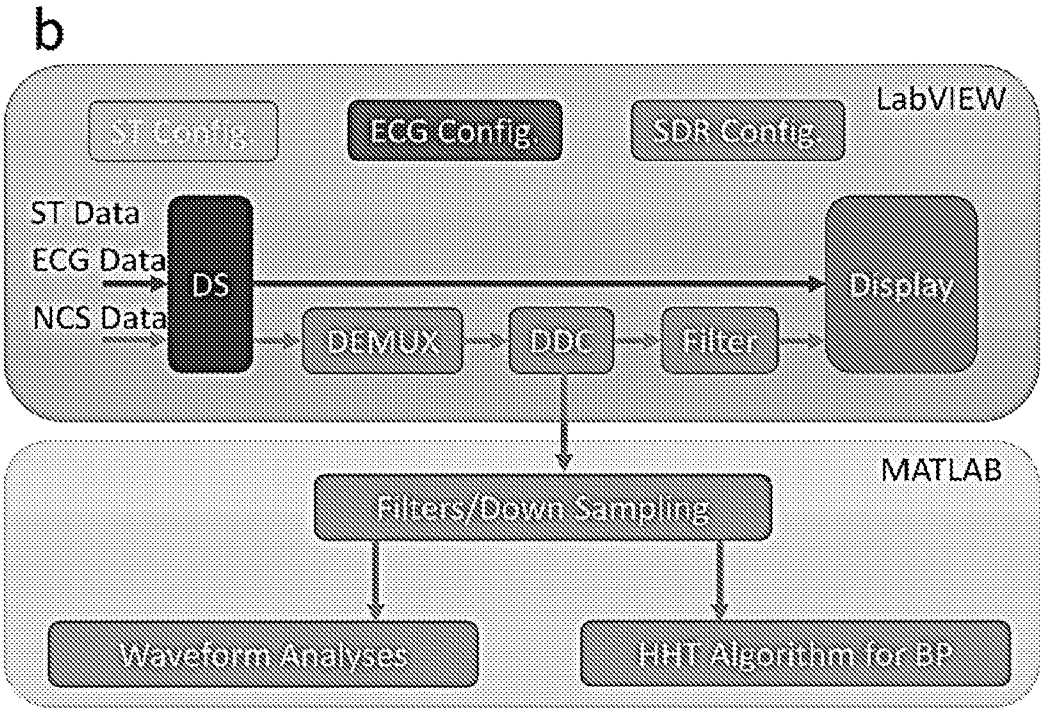
Fig. 18

NEAR-FIELD COHERENT SENSING METHODS AND SYSTEMS

CROSS-REFERENCE TO RELATED APPLICATIONS

This application claims priority to U.S. Provisional Application No. 62/824,261, filed on Mar. 26, 2019, and 62/824,268, filed on Mar. 26, 2019, and 62/955,994, filed on Dec. 31, 2019, the disclosures of which are incorporated herein by reference.

STATEMENT REGARDING FEDERALLY SPONSORED RESEARCH

This invention was made with government support under contract nos. DE-AR0000528 and DE-AR0000946 awarded by the Department of Energy and under award no. W81XWH-19-1-0004 by the U.S. Army Medical Research Acquisition Activity Office of the Department of Defense. The government has certain rights in the invention.

FIELD OF THE DISCLOSURE

The present disclosure relates to detection of motion, and in particular, detecting vital signs without a need for physical contact.

BACKGROUND OF THE DISCLOSURE

Vital-sign monitoring is an important technology for e-health, assisted living, driver alertness, wearables, and the Internet of Things (IoT). Current personal devices can provide heartbeat information through electrocardiogram (ECG) and photo-plethysmography (PPG) with direct skin contact. However, these devices cannot detect heart sounds or other determine other vital signs such as blood pressure. These devices also require the user to carry an extra device (e.g., a watch, etc.) and do not provide an “invisible” (non-intrusive) technique for determining or monitoring vital signs. The continues to be a need for sensors which are less invasive and/or include functionality not found in other devices.

BRIEF SUMMARY OF THE DISCLOSURE

Active near-field coherent sensing (NCS) systems to monitor vital signs are introduced herein. In some embodiments, the system is integrated into a seat, such as, for example, a vehicle seat. The system may monitor the vital signs of a seat occupant with multiple sensing points. The sensor can be integrated into the cushion and hence “invisible” to the user. People spend enormous amounts of time in some forms of sitting during work, leisure, driving, and talking. Thus, the need for extra wearable devices can be avoided if vital-sign sensing systems can be integrated into the structures of sofas, vehicle seats, lounge chairs, office chairs, etc., any of which may be generally characterized as a seat, or integrated into a structure attachable to or usable in combination with such structures (e.g, a sensor mat or applique that can be lain across or attached to a seat, a sensor system attachable to a seat, a sensor system insertable within a seat, etc.). In other examples, the present concepts could be realized as a wearable vital-sign sensing system, either as a stand-alone system worn under clothing or a vital-sign sensing system integrated into one or more wearables (e.g., garments, undergarments, outerwear, headwear, footwear, etc.)

In other embodiments, the present disclosure provides a passive harmonic RFID (radio-frequency identification) tag as a heartbeat sensor. A frequency strategy of antenna impedance matching is provided to increase the energy coupling deep into the motion source that produces the heart sound. The previously-described near-field coherent sensing (NCS) technique can provide improved signal quality and touchless operation, but the present disclosure provides improvements in coupling to the sound source and with the transceiver sensitivity and SNR, which are advantageous for accurate retrieval of the feeble heart sound. A cancellation network (e.g., an adaptive bridge circuit) is provided to balance the NCS-modulated and non-modulated signals, which can significantly improve the sensing dynamic range. The present disclosure provides a multiple-input-multiple-output (MIMO) near-field coherent sensing (NCS) system that can derive detailed motion and pressure dynamics of a heartbeat, including independent systolic and diastolic blood pressure as well as the heart sound.

DESCRIPTION OF THE DRAWINGS

For a fuller understanding of the nature and objects of the disclosure, reference should be made to the following detailed description taken in conjunction with the accompanying drawings.

FIG. 6. Blood pressure analyses based on an NCS signal during the systole phase. (a) A diagram showing a cross section of the heart ejecting blood from the left and right ventricles. (b) A Wiggers Diagram showing an expected relation between an ECG and the aortic pressure. (c) A Hilbert-Huang transform (HHT) analysis of $C_{11}$ when the person was seated on the floor. The synchronized ECG signal indicates the timing. (d) $C_{11}$ HHT when the person took a standing posture. (e) $C_{33}$ HHT for the pulmonary cycle when the person held their breath after maximum exhalation. (f) $C_{33}$ HHT when the person held breath after maximum inhalation.

FIG. 18. Diagrams of a test embodiment of the present disclosure including stethoscope, ECG, and NCS information. (a) Electronic hardware. (b) Software function blocks and data flow.

DETAILED DESCRIPTION OF THE DISCLOSURE

The present disclosure may be embodied as a method for near-field coherent sensing ("NCS"), which modulates the movement of an individual onto radio frequency ("RF") signals, which can be multiplexed RF signals. Using NCS methods, RF energy in, for example, the ultra-high frequency (UHF) band (300 MHz-3 GHz) can be coupled into the body, and detailed dielectric boundary motion in the near-field region of the sensing antenna can be retrieved. Movements of an individual may include, for example, movements related to vital signs—e.g., heartbeat, pulse, breathing, etc. Embodiments of the present method may directly modulate mechanical motion on the body surface or inside the body of the individual onto RF signals in the near-field range. The motion can be modulated onto multiplexed harmonic RF Identification ("RFID") backscattering signals with unique digital identification ("ID"). At the same time, the radiation level utilized is well under the safety standard prescribed by OSHA (Occupational Safety and Health Administration).

The "near field" of an antenna is a region where induction characteristics dominate over radiation characteristics and the relationship between the electric field (E field) and the magnetic field (H field) has not reached the far-field superposition of plane waves. In embodiments of the present disclosure, "near-field" may refer to the close-in region of an antenna where angular field distribution is dependent upon the distance from the antenna. In embodiments, the near-field extends to the region within one wavelength (λ) of the antenna. In other embodiments, the near-field extends to the region within λ/2, λ/3, λ/4, or λ/2π of the antenna, where λ is the operating wavelength of the antenna in the dielectric material(s) under consideration. Other embodiments will be apparent to one having skill in the art with the benefit of the present disclosure.

Figure 2:
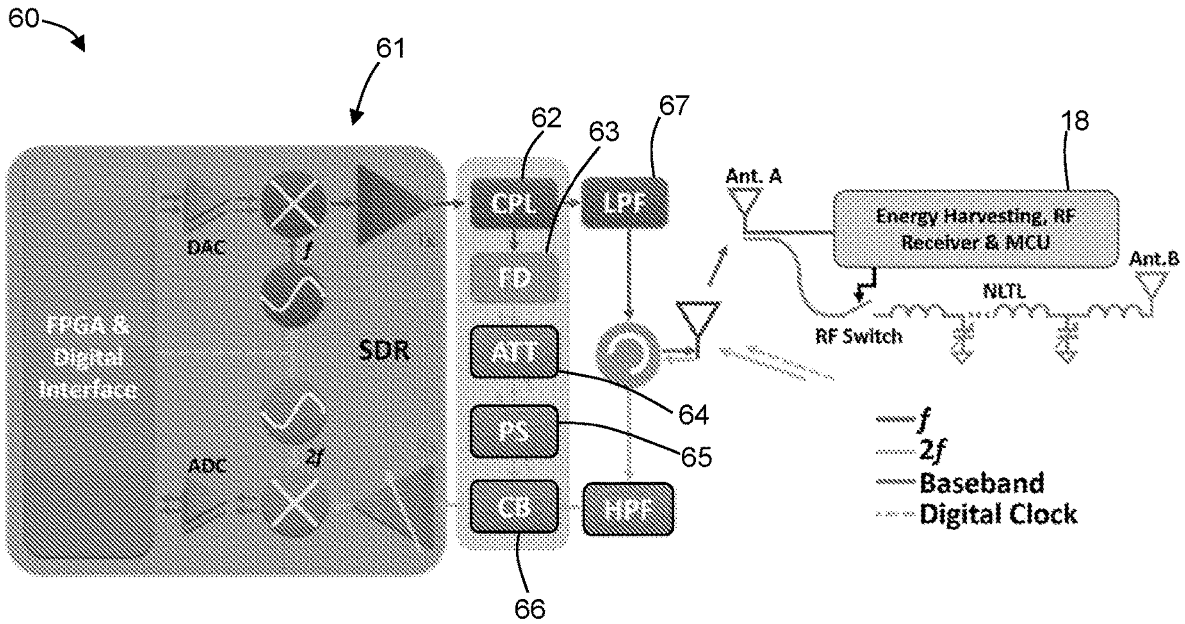
FIG. 2. The NCS experimental setup with a passive sensing RFID tag in the front pocket on the chest area. DAC: digital to analog converter; ADC: analog to digital converter; SDR: software de-fined radio; CPL: coupler; FD: frequency doubler; ATT: tunable attenuator; PS: phase shifter; CB: combiner; LPF: low-pass filter; HPF: high-pass filter; NLTL: non-linear transmission line.
Figure 3:
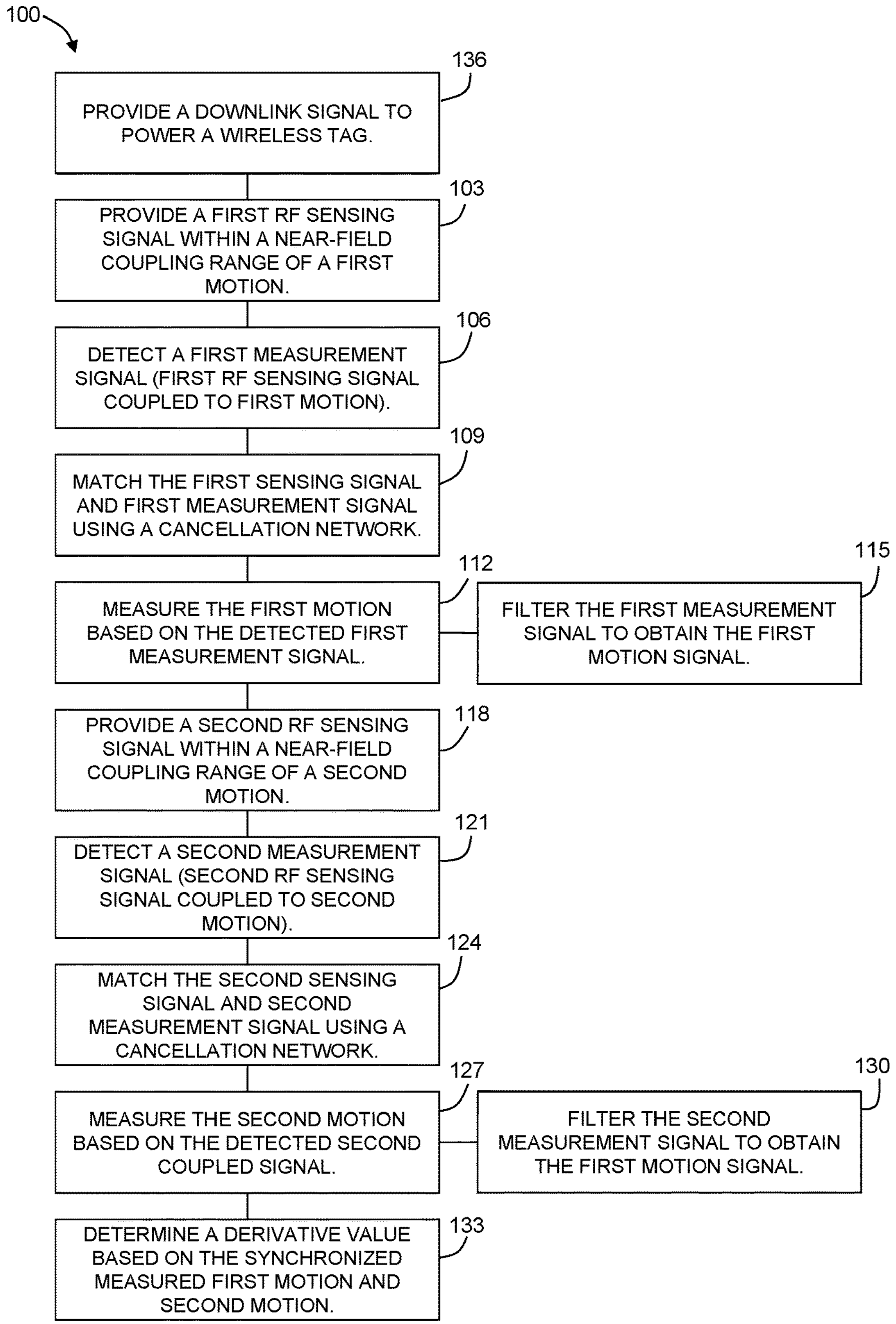
FIG. 3. A chart depicting a method according to an embodiment of the present disclosure.

With reference to FIG. 2, in a first aspect, an NCS method is provided for non-contact measurement of an on-body and/or inside-body motion of an individual. The individual may be, for example, a human or a non-human animal. The detected motion may be, for example, a heart motion, a pulse, a respiration motion, a bowel motion, an eye motion, or other body motion as will be apparent in light of the present disclosure. Embodiments of the present method 100 may directly modulate the mechanical motion on the body surface or inside the body of the individual onto multiplexed radio signals integrated with a unique digital ID. A first radiofrequency ("RF") sensing signal is provided 103 within a near-field coupling range of a first motion (the first location) to be measured to generate a first measurement signal (the first sensing signal modulated by the first motion). The provided 103 first sensing signal may be an ID-modulated signal. In some embodiments, the first sensing signal is an active radio link. In some embodiments, the first sensing signal is a backscattered RFID link. For example, an antenna may emit a beacon or ID-modulated sensing signal in either an active radio link or a backscattering RFID (radio identification) link. The first sensing signal will be modulated by the first motion thereby generating a first measurement signal. The method 100 includes detecting 106 the first measurement signal using a first receiver. In some embodiments, the detection 106 may be done at the far field, for example, detecting the first measurement signal transmitted through the body of the individual. In some embodiments, the detection 106 is of a reflected signal, for example, using the near-field antenna.

The first sensing signal and the first measurement signal are matched 109 using a cancellation network. In this way, any first sensing signal (i.e., non-modulated first sensing signal) detected with the first measurement signal may be reduced. The first motion is measured 112 based on the first measurement signal with reduced non-modulated first sensing signal. In NCS, more energy is directed into the body tissue than previous techniques, so the backscattered signal from internal organs is implicitly amplified. Also, shorter wavelengths within the body tissues render a small mechanical motion into a relatively large phase variation. Shorter wavelengths within the body of the individual naturally increase the signal-to-noise ratio ("SNR"). The differential nature of in-body signals can isolate large surface movements. This can also increase sensitivity, enabling the measurement of a weak motion signal such as, for example, a wrist pulse. Because the internal mechanical motion modulation gives a differential signal similar to an interferometer, the common signal caused by external movement can be readily depressed by filtering. With an antenna within the near-field coupling range of the mechanical motion inside the body, the propagating or reflected wave can be readily detected in a coherent manner and will contain the real-time geometric-average information of the mechanical motion. The motion may be measured by filtering 115 the first measurement signal to obtain a motion signal. For example, measuring 112 the first motion may include bandpass filtering the first measurement signal using a frequency range corresponding to cardiac motion. In the case of ID-modulated wave, multiple mechanical motions may be read simultaneously in a synchronized manner using multiple devices. Multiplexing techniques can be used in passive backscattering or active radio transmission to facilitate simultaneous sensing at multiple points and/or for multiple persons.

In some embodiments, a second RF sensing signal is provided 118 within a near-field coupling range of a second motion to be measured (the second location). In this way, a second measurement signal is generated (the second sensing signal modulated by the second motion). Similar to the first sensing signal, the second sensing signal (and any additional sensing signals as described below) may be an ID-modulated signal. In some embodiments, the second sensing signal is an active radio link. In some embodiments, the second sensing signal is a backscattered RFID link. For example, an antenna may emit a beacon or ID-modulated second sensing signal in either an active radio link or a backscattering RFID (radio identification) link. The method 100 includes detecting 121 the second measurement signal using a second receiver. In some embodiments, the detection 121 may be done at the far field, for example, detecting the second measurement signal transmitted through the body of the individual. In some embodiments, the detection 121 is of a reflected signal, for example, using the near-field antenna. The second sensing signal and the second measurement signal are matched 124 using a cancellation network. In this way, any second sensing signal (i.e., non-modulated second sensing signal) detected with the second measurement signal may be reduced. The second motion is measured 127 based on the second measurement signal with reduced non-modulated second sensing signal. The second motion may be measured by filtering 130 the second measurement signal to obtain a second motion signal. A derivative value may be determined 133 based on the synchronized measured first motion and second motion. For example, where the first motion is a heartbeat (measured near the chest) and the second motion is a pulse (measured near the wrist), the derivative value may be a blood pressure determined 133 based on the heartbeat and the pulse.

In some embodiments, a cross-coupled measurement signal is detected. For example, a cross-coupled measurement signal may be a motion-modulated second sensing signal detected using the first receiver (referred to herein as a "two-one" cross-coupled measurement signal or "2-1" measurement signal). In this way, the first sensing signal is modulated by motion between the first location and the second receiver to measure an additional motion. Additionally or alternatively, a 1-2 cross-coupled signal may be detected—the motion-modulated first sensing signal detected using the second receiver.

In some embodiments, more than two locations may be used. For example, a method for measuring heart dynamics may include providing two or more RF sensing signals each at a location which is different than the others, as further described below under the heading "Heart Measurement." In this way, corresponding measurement signals are generated (the two or more sensing signals modulated by the heart at their respective locations). Each measurement signal can be detected at its corresponding location and cross channels. The heart motion is measured based on each measurement signal.

In some embodiments, the first RF sensing signal is provided from a wireless tag. For example, a downlink signal may be provided 136 to power a wireless tag. The first RF sensing signal is provided 103 from the wireless tag within a near-field coupling range of the first motion to be measured. The first downlink signal may have a frequency—the downlink frequency. The first sensing signal may have a frequency—the first sensing frequency—that is a harmonic of the downlink frequency. For example, the first sensing frequency may be the second harmonic of the downlink frequency. The wireless tag may be, for example, a harmonic radio-frequency identification (RFID) tag or an RFID tag with subcarrier modulation.

In embodiments of the present disclosure, the transmitting and receiving frequencies are coherent. For example, where the tag is a wireless tag, the downlink frequency and the first sensing frequency are coherent.

Figure 1:
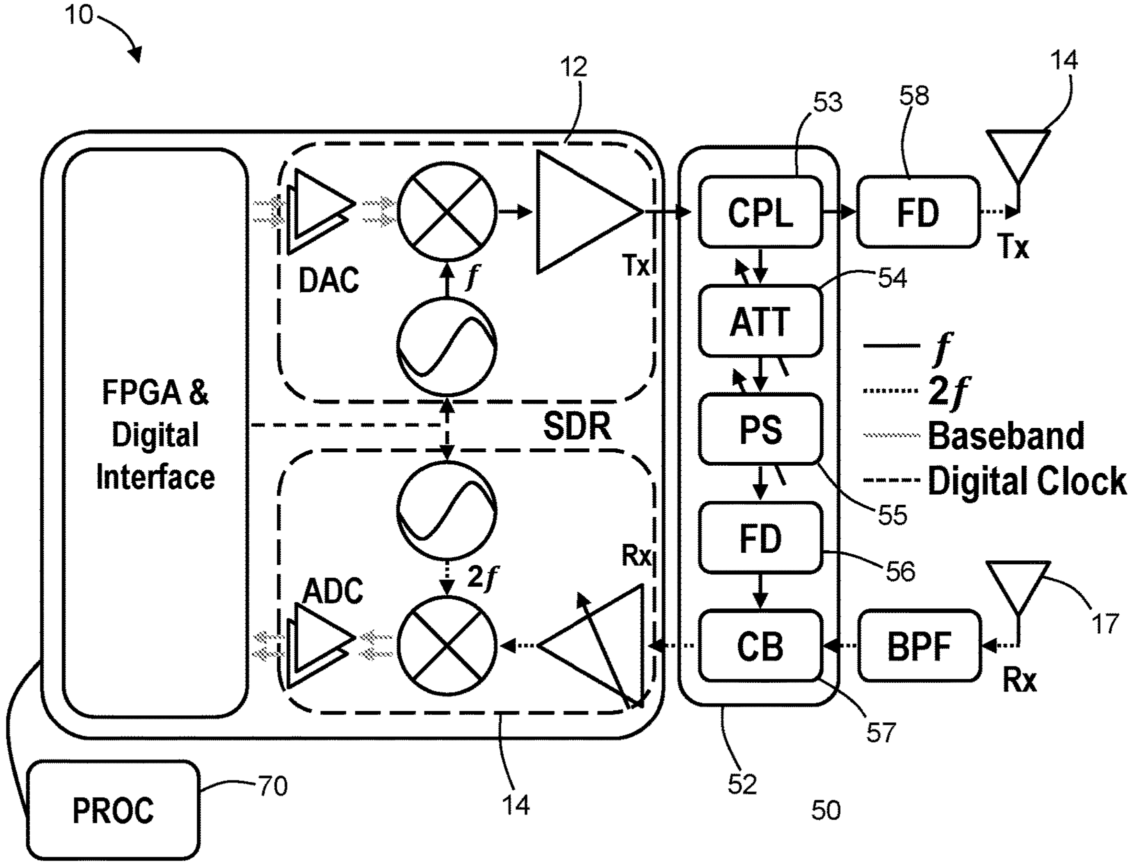
FIG. 1. The block diagram of a single-channel active NCS system with the balancing bridge to maximize the vital-sign sensitivity.

In another aspect, the present disclosure may be embodied as a system 10 for measuring motion of an individual (see, e.g., FIG. 1). The system 10 includes a first signal source 12 for generating a first sensing signal. A first Tx antenna 14 is in electrical communication with the first signal source 12. The first Tx antenna 14 is configured to be disposed within a near-field coupling range of a first motion to be measured. For example, the first Tx antenna 14 may be configured to be disposed within a coupling range of a heart motion, a pulse, a respiration motion, a bowel motion, an eye motion, etc. In this way, a first measurement signal is generated by the first sensing signal being modulated by the first motion. The first sensing signal may be an ID-modulated wave. For example, the EM wave may be an active radio link or a backscattering RFID link.

The system includes a first receiver 16 for detecting the first measurement signal (the first sensing signal coupled with (i.e., modulated by) the first motion) and a first Rx antenna 17 in communication with the first receiver 16. The first receiver and/or the first Rx antenna may be configured to detect the first measurement signal as a transmitted signal—i.e., far-field radiation. The first receiver and/or the first Rx antenna may be configured to detect the first measurement signal as a reflected signal—i.e., antenna reflection. The system may include a filter in communication with the first receiver, wherein the filter is configured to demodulate and filter the first measurement signal to obtain a motion signal. The filter may be, for example, a processor (such as a digital-signal processor ("DSP")) programmed to sample, demodulate, and/or filter the first measurement signal to derive the motion signal. The filter may be or may include a bandpass filter configured to filter the first measurement signal using a first frequency range corresponding to the first motion.

The system 10 further includes a signal processing circuit 50 configured to match the first sensing signal and the first measurement signal. The signal processing circuit 50 may comprise a cancellation network 52. An exemplary cancellation network includes a coupler 53 configured to receive the first sensing signal from the first signal source, an attenuator 54 configured to attenuate the amplitude of the first sensing signal based on feedback information, a phase shifter 55 configured to shift the phase of the first sensing signal based on the feedback information, a frequency doubler 56 configured to double a frequency of the first sensing signal, and a combiner 57 configured to match the modified first sensing signal with the first measurement signal. Further discussion of the signal processing circuit and cancellation network are provided below. In some embodiments, the first sensing signal is a frequency-doubled downlink frequency. For example, FIG. 1 shows a Tx frequency doubler 58 which doubles a downlink frequency before transmission via Tx antenna 14.

In some embodiments, the first Tx antenna is configured to be disposed within a coupling range of a heart motion, a pulse, and/or a respiration motion. In some embodiments, the first Tx antenna and the first Rx antenna are disposed within a seat, for example, as further discussed below under the heading "Seat Integration."

Figure 4:
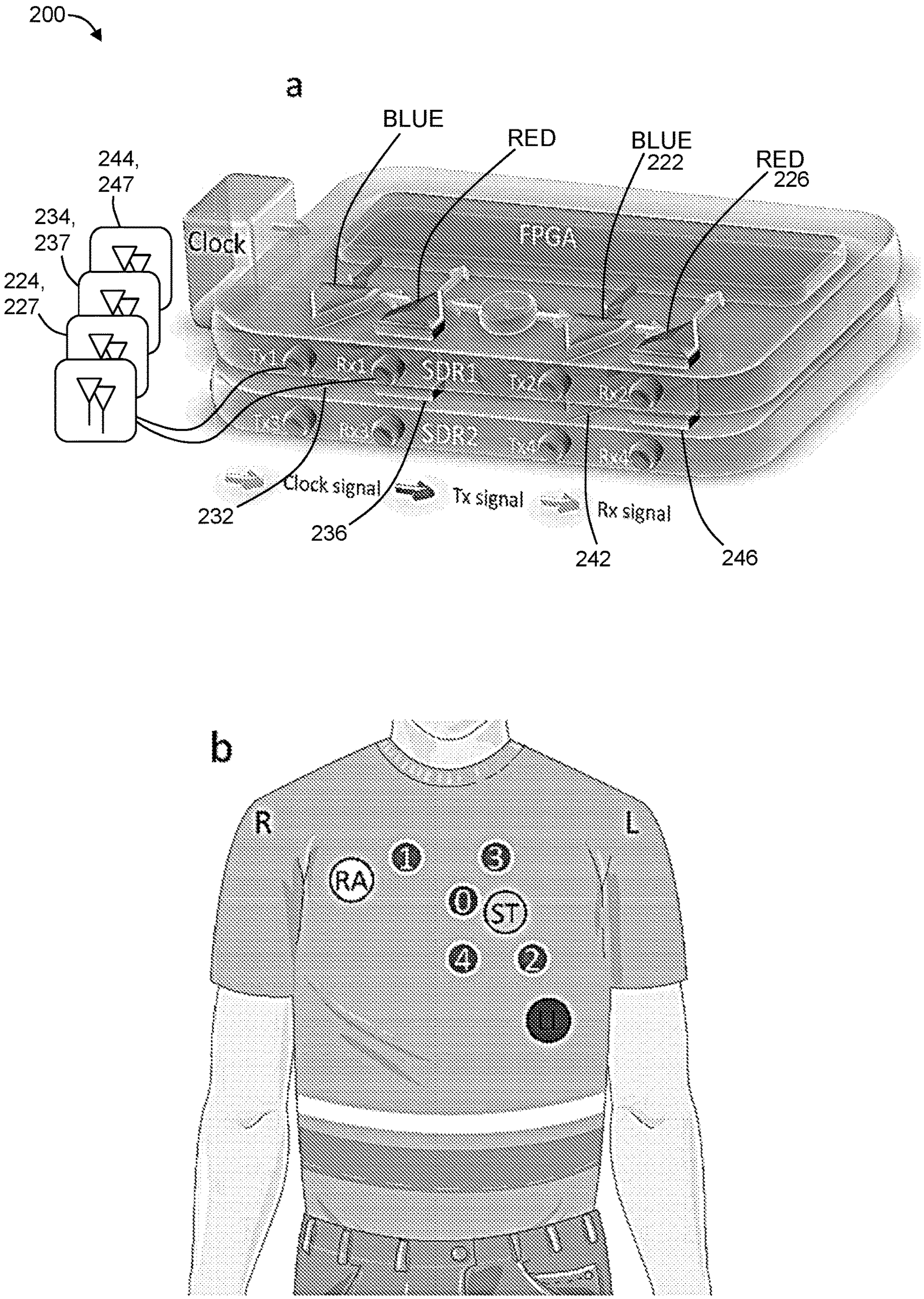
FIG. 4. An exemplary multi-static MIMO NCS system according to an embodiment of the present disclosure. (a) Electronic hardware: A reader constructed using two SDRs and an external reference clock source for synchronization. FPGA denotes the field-programmable gate array; Tx the transmitter; Rx the receiver. (b) Body placement: The location of the sensing points in the exemplary system: Points 0 to 4 are for NCS, ST is the stethoscope drum placement, and the ECG electrodes are positioned at LL and RA. The letters “L” and “R” indicate body left and right.

The system 200 may include a second signal source 222 for generating a second sensing signal (see, e.g., FIG. 4). A second Tx antenna 224 may be in electrical communication with the second signal source 222. The second Tx antenna 224 is configured to be disposed within a near-field coupling range of a second motion to be measured. For example, the second Tx antenna 224 may be configured to be disposed within a coupling range of a heart motion, a pulse, a respiration motion, a bowel motion, an eye motion, etc. In this way, a second measurement signal is generated by the second sensing signal being modulated by the second motion. The second sensing signal may be an ID-modulated wave. For example, the EM wave may be an active radio link or a backscattering RFID link.

The system may further include a second receiver 226 for detecting the second measurement signal (the second sensing signal coupled with (i.e., modulated by) the second motion) and a second Rx antenna 227 in communication with the second receiver 226. The second receiver and/or second first Rx antenna may be configured to detect the second measurement signal as a transmitted signal—i.e., far-field radiation. The second receiver and/or the second Rx antenna may be configured to detect the second measurement signal as a reflected signal—i.e., antenna reflection. The signal processing circuit may be further configured to match the second sensing signal and the second measurement signal. In some embodiments, the signal processing circuit may include a second cancellation network for processing the second sensing signal and the second measurement signal.

In some embodiments, the first receiver may be configured to detect a cross-coupled measurement signal based on the second sensing signal. For example, the first receiver may detect a 2-1 cross-coupled measurement signal (the second sensing signal modulated by additional motion between the first Rx antenna and the second Tx antenna). In some embodiments, the second receiver may be configured to detect a 1-2 cross-coupled measurement signal.

The system 200 may include a third signal source 232 for generating a third sensing signal. A third Tx antenna 234 may be in electrical communication with the third signal source 232. The third Tx antenna 234 is configured to be disposed within a near-field coupling range of a third motion to be measured. For example, the third Tx antenna 234 may be configured to be disposed within a coupling range of a heart motion, a pulse, a respiration motion, a bowel motion, an eye motion, etc. In this way, a third measurement signal is generated by the third sensing signal being modulated by the third motion. The third sensing signal may be an ID-modulated wave. For example, the EM wave may be an active radio link or a backscattering RFID link.

The system may further include a third receiver 236 for detecting the third measurement signal (the third sensing signal coupled with (i.e., modulated by) the third motion) and a third Rx antenna 237 in communication with the third receiver 236 The third receiver and/or third first Rx antenna may be configured to detect the third measurement signal as a transmitted signal—i.e., far-field radiation. The third receiver and/or the third Rx antenna may be configured to detect the third measurement signal as a reflected signal—i.e., antenna reflection. The signal processing circuit may be further configured to match the third sensing signal and the third measurement signal. In some embodiments, the signal processing circuit may include a third cancellation network for processing the third sensing signal and the third measurement signal.

The system 200 may include a fourth signal source 242 for generating a fourth sensing signal. A fourth Tx antenna 244 may be in electrical communication with the fourth signal source 242. The fourth Tx antenna 244 is configured to be disposed within a near-field coupling range of a fourth motion to be measured. For example, the fourth Tx antenna 244 may be configured to be disposed within a coupling range of a heart motion, a pulse, a respiration motion, a bowel motion, an eye motion, etc. In this way, a fourth measurement signal is generated by the fourth sensing signal being modulated by the fourth motion. The fourth sensing signal may be an ID-modulated wave. For example, the EM wave may be an active radio link or a backscattering RFID link.

The system may further include a fourth receiver 246 for detecting the fourth measurement signal (the fourth sensing signal coupled with (i.e., modulated by) the fourth motion) and a fourth Rx antenna 247 in communication with the fourth receiver 246. The fourth receiver and/or fourth first Rx antenna may be configured to detect the fourth measurement signal as a transmitted signal—i.e., far-field radiation. The fourth receiver and/or the fourth Rx antenna may be configured to detect the fourth measurement signal as a reflected signal—i.e., antenna reflection. The signal processing circuit may be further configured to match the fourth sensing signal and the fourth measurement signal. In some embodiments, the signal processing circuit may include a fourth cancellation network for processing the fourth sensing signal and the fourth measurement signal.

One or more of the first, second, third, and fourth receivers may be configured to detect cross-coupled measurement signals. For example, the first receiver may be configured to detect a cross-coupled measurement signal based on the third sensing signal (the 3-1 cross-coupled measurement signal); the first receiver may be configured to detect a cross-coupled measurement signal based on the fourth sensing signal (the 4-1 cross-coupled measurement signal); the second receiver may detect cross-coupled measurement signals based on one or more of the first sensing signal, third sensing signal, and fourth sensing signal; and so on. Such multiple-in, multiple-out (MIMO) configurations are further discussed below.

In some embodiments, such as the system 60 depicted in FIG. 2, the first signal source may be a wireless tag 18. A first downlink source 62 may be provided for generating a downlink signal. The first downlink signal may have a first downlink frequency. The wireless tag may be configured to receive the first downlink signal and generate the first sensing signal. In some embodiments, the first sensing signal has a frequency which is a harmonic of the first downlink frequency. For example, the first sensing signal frequency may be a second harmonic of the first downlink frequency. The wireless tag may be configured to be powered by the downlink signal. For example, the wireless tag may include an energy-harvesting circuit configured to power the wireless tag using the first downlink signal.

Some embodiments of the present disclosure include a processor 70. In some embodiments, the processor is configured to determine a blood pressure based on the first measurement signal. In some embodiments, the processor is configured to confirm the identity of a person. For example, the processor may confirm the identity of a person based on a dynamic time warping (DTW) distance of a cross-coupled measurement signal of the person as further described below.

Heart Measurement

Auscultatory stethoscopes have been a standard diagnostic tool for cardiopulmonary functions for more than 200 years. Thanks to the high sensitivity and large dynamic range for acoustic signal processing by human or devices, detailed heart sound at the S1 and S2 points of the cardiogram can be retrieved. However, because of the large acoustic impedance mismatching in various materials, especially for air gaps, the transducing diaphragm or bell of the stethoscope needs to be in tight skin touch for best signal quality. The sensation of the practice thus causes concerns for comfort and privacy, which discourages long-term daily monitoring. Other cardiovascular tools such as electrocardiogram (ECG) and photo-plethysmography (PPG) cannot detect the heart sound, although simultaneous measurements can provide clues of S1 and S2 timing. Radar-based methods based on radio frequency (RF) for heartbeats have been investigated, but the signal quality is limited by strong respiration interference and low signal-to-noise ratio (SNR) from minute chest surface vibration. The system dynamic range is often poor due to strong self-jamming. Thus, most of these radar-based methods can only recover the fundamental heartbeat and its variation, not the heart sound. Through meticulous signal processing, some part of the heart sound can be detected, but the signal quality is worse than the conventional stethoscope.

A heart sound is faint and embedded in a strong fundamental tone of the heartbeat. The heart sound may also be embedded in the large respiration motion if the individual does not hold his or her breath. Retrieval of the heart sound requires signal transducing and processing modules that are highly efficient and low noise.

Embodiments of the present disclosure may be used for heart measurement. For example, the first RF sensing signal may be provided proximate to an aortic valve of the heart, and the second RF sensing signal may be provided proximate to a mitral valve of the heart. A third RF sensing signal may be provided proximate to a pulmonary valve of the heart. A fourth RF sensing signal may be provided proximate to a tricuspid valve of the heart. With multiple RF sensing signals, corresponding measurement signals may be detected. Similarly, one or more cross-coupled measurement signals may be detected (e.g., the fourth sensing signal detected at the second receiver, etc.) One or more heart motions may be measured based on the measurement signals and/or the one or more cross-coupled measurement signals.

The present disclosure may be embodied as a method for non-contact measurement of a body motion of an individual (e.g., on-body or inside-body motion). The individual may be, for example, a human or a non-human animal. The detected motion may be, for example, a heart motion, a pulse, a respiration motion, a bowel motion, an eye motion, or other body motion as will be apparent in light of the present disclosure. A downlink signal is provided to power a wireless tag. A first radiofrequency ("RF") sensing signal is provided from the wireless tag within a near-field coupling range of a first motion to be measured to generate a measurement signal. The first sensing signal may be an ID-modulated signal. The first sensing signal may be a backscattered RFID link. The first sensing signal will be modulated by the first motion thereby generating a first measurement signal. The method includes detecting the first measurement signal. For example, using an antenna of an RFID reader may be used to detect a reflected signal. With an antenna within the near-field coupling range of the mechanical motion inside the body, the reflected wave can be readily detected in a coherent manner and will contain information of the mechanical motion.

The first sensing signal is matched to the first measurement signal using a cancellation network as further described below. The cancellation network is used to reduce any non-modulated first sensing signal that is detected along with the first measurement signal. The first motion is measured based on the first measurement signal with reduced non-modulated first sensing signal. In some embodiments, feedback information is obtained from the first measurement signal through timing and magnitude. The first sensing signal is matched with the first measurement signal based on the feedback information to obtain a combined signal. The combined signal is demodulated to obtain the first motion signal. Measuring the first motion may further comprise filtering the first measurement signal using a first frequency range corresponding to the first motion. In some embodiments, a second motion is measured by, for example, filtering the first measurement signal using a second frequency range corresponding to the second motion.

The present disclosure may be embodied as a system for measuring motion of an individual. The system includes a first signal source for generating a downlink signal. A first antenna is in electrical communication with the first signal source. The first signal source and first antenna may be a part of an RFID reader. A wireless tag includes a second antenna configured to receive the first downlink signal. The wireless tag may include a third antenna to provide a first sensing signal. The wireless tag and/or the third antenna is configured to be disposed within a near-field coupling range of a first motion to be measured. For example, the wireless tag may be configured to be disposed within a coupling range of a heart motion, a pulse, a respiration motion, a bowel motion, etc. In this way, the first measurement signal is generated as the first sensing signal modulated by the first motion.

The system includes a first receiver for detecting the first measurement signal (the first sensing signal coupled with (modulated by) the first motion). The first receiver may be in electrical communication with the first antenna. The first antenna may be configured to receive the first measurement signal as reflected by the body of the individual. A signal processing circuit is configured to match the first sensing signal and the first measurement signal as further described herein. The signal processing circuit may be, for example, a cancellation network. The cancellation network may be configured to reduce in-band self-jamming interferences. In some embodiments, the cancellation network may include a coupler configured to receive the first sensing signal from the first signal source; an attenuator configured to attenuate the amplitude of the first sensing signal based on feedback information; a phase shifter configured to shift the phase of the first sensing signal based on the feedback information; a frequency doubler configured to double a frequency of the first sensing signal; and a combiner configured to match the modified first sensing signal with the first measurement signal. The system may include a bandpass filter configured to filter the first measurement signal using a first frequency range corresponding to the first motion.

The signal processing circuit may be, for example, a processor (such as a digital-signal processor ("DSP")) programmed to sample, demodulate, and/or filter the first measurement signal to derive the motion signal.

In some embodiments, wireless tags, such as passive (i.e., having no local power source such as a battery) RFID tags, may be integrated into garments near areas where vital signs are to be measured. Such RFID tags may provide for an NCS implementation with low deployment and maintenance costs. Such RFID tags may provide ID-modulated signals where a unique ID of each tag helps discriminate its signal against interference from other tags and ambient signals.

To strongly couple to the sound source deep in the heart tissues, microwave signals in the ultrahigh frequency (UHF) band (300 MHz-3 GHz) were employed due to their reasonably small attenuation inside the human body, and were determined to have effective signal transduction if the sensing antenna can be properly designed and placed. To study the antenna and frequency effects, a human torso electromagnetic (EM) simulation model was constructed in CST Microwave Studio. The internal organ geometry and tissue property of the human torso were extracted from the Zubal Phantom as is known in the art. Within the near-field region determined by the selected frequency, the sensing antenna can be placed close to the left pectoral major area and can be placed over layers of clothing without needing to touch the skin. However, the proximity of the human tissue with high dielectric constant can detune the antenna, resulting in significant changes in the S parameters in both transmission towards the body and the antenna reflection. The radiation pattern would change as well.

In view of the system design, the antenna can be considered as the matching component between the RF impedance (often around 50Ω) and the impedance of the joint region of the free space and the torso. For the CST simulation shown in FIG. 19(*a*), $S_{11}$ of a 2 GHz dipole antenna is shown as the solid line when the antenna operates in the free space. However, when that antenna is placed near the chest area, $S_{11}$ will be shifted to the dotted line, which means the frequency near 2 GHz can no longer have good emission efficiency due to high reflection. To better couple into the heart sound source deep inside the torso volume, one can either shift the operation frequency to a band with low $S_{11}$, or redesign the antenna geometry to fit the original 2 GHz band. The dashed line of FIG. 16(*a*) is an exemplary redesigned antenna matched with the torso placement. The graph shows that the reflection at 2 GHz is improved from −3 dB to −18 dB.

Figure 16:
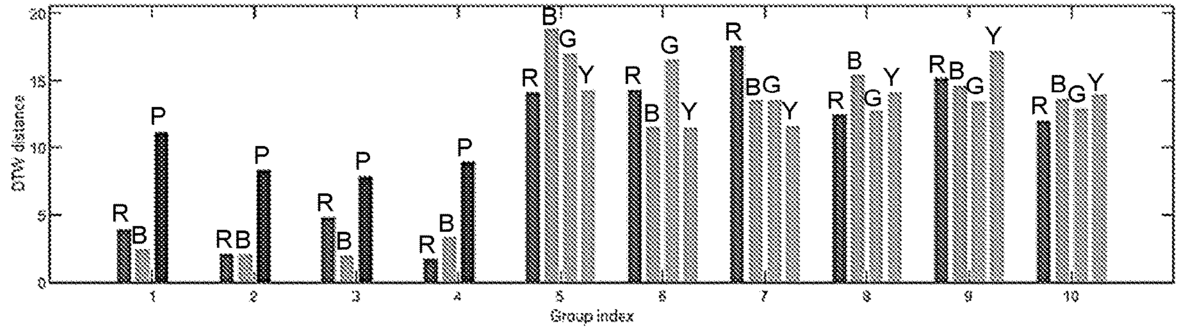
FIG. 16. A graph showing correlation of the cross-port channels by the DTW distances calculated in 10 groups. Groups 1-4: $C_{21}$, $C_{12}$, $C_{43}$ and $C_{34}$. Groups 5-10: Comparison between each pair of ($C_{21}$, $C_{12}$), ($C_{21}$, $C_{43}$), ($C_{21}$, $C_{34}$), ($C_{12}$, $C_{43}$), ($C_{12}$, $C_{34}$), and ($C_{43}$, $C_{34}$). The red bar (marked 'R' in the figure) represents the DTW distance from all measurements of the first person, the blue bar (marked 'B' in the figure) the DTW distance from all measurements of the second person, the purple bar (marked 'P' in the figure) between the templates of the two persons, the green bar (marked 'G' in the figure) the DTW distance between the template of the first channel of the first person and the second channel of the second person, and the yellow bar (marked 'Y' in the figure) the DTW distance between the template of the second channel of the first person and the first channel of the second person.
Figure 19:
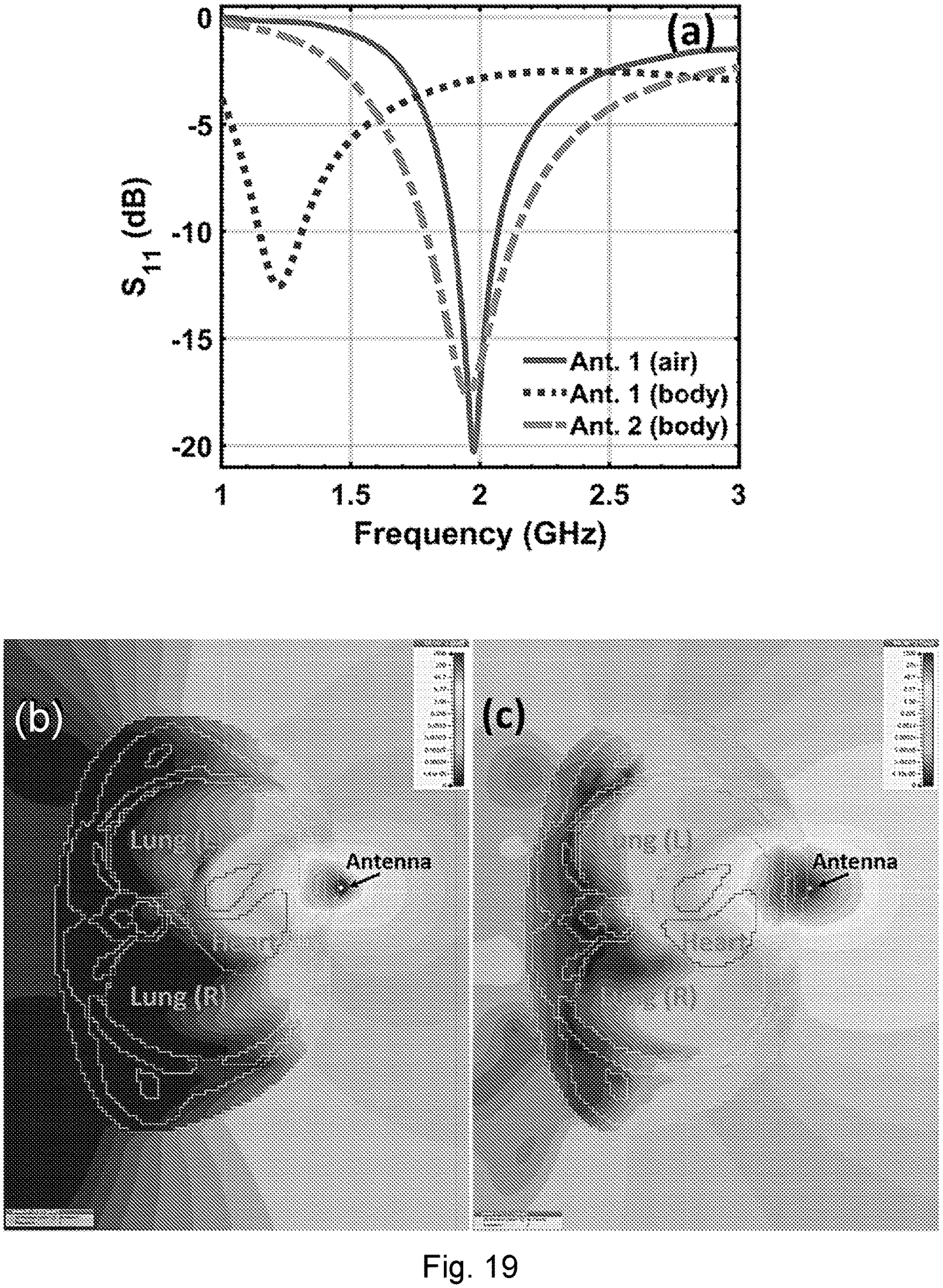
FIG. 19. Simulated NCS antenna detuning and body coupling. (a) Sri of an antenna designed to operate at 2 GHz in free air, and the corresponding detuning with chest placement; (b) EM power flow at 2 GHz of the NCS signal coupled into the human torso with poor impedance matching, and (c) with proper impedance matching.

To further demonstrate the deep coupling to the internal organs, FIGS. 19(*b, c*) show the power flow at 2 GHz with the chest antenna in FIG. 16(*a*). For the original antenna with poor impedance match (the dotted line), little RF energy is coupled to the heart, while the revised antenna (the dashed line) can provide stronger coupling which also increases the total strength of the backscattered signal. Hence, with the same noise floor, both SNR and sensitivity will be improved.

Another aspect that can affect the heart sound quality is the signal dynamic range. There are two signal paths received by the reader: the signal modulated by the internal heartbeat and the non-modulated backscattering RF signal. Based on the NCS setup described above, the two parts are coherent and the internal motion can be derived from the demodulated amplitude, similar to the interferometer structure. However, the received signal strength (RSS) of the non-modulated signal is usually much larger than the modulated part due to the antenna directivity, coupling efficiency, reflection coefficient, and energy loss caused by human tissue. Hence, the low noise amplifier (LNA) at the receiver (Rx) front end can be easily saturated by the non-modulated signal, i.e., the Rx gain added to the modulated signal is limited by the high level of the non-modulated signal. Even though the harmonic sensing RFID can provide high isolation between the transmitter (Tx) and Rx to boost the system SNR, the sensitivity limitation originated from the finite Rx dynamic range can be relieved if the NCS-modulated and non-modulated signals can be balanced before the LNA.

The present device includes a cancellation network (e.g, balance bridge structure) inserted to adaptively compensate the amplitude and phase of the non-modulated signal. FIG. 2 shows an embodiment using a software defined radio (SDR) configured as a harmonic RFID reader, where the local oscillator of the Rx is twice the frequency of the Tx and shares the same clock source. The Tx signal goes through a 10 dB coupler (CPL) 62, and the major part of the energy passes through the low-pass filter (LPF) 67 and the circulator 68 and is transmitted by the dual band antenna. A harmonic RFID tag 18 is placed, for example, near the chest area to sense the heartbeat. The downlink wireless signal at frequency f is received by antenna A of the tag. Part of the energy of the received signal is harvested and the other part is coupled to the nonlinear transmission line (NLTL) to generate a harmonic signal as the sensing signal, which is transmitted out by antenna B of the harmonic tag. In FIG. 2, the NCS-modulated RF signal is the dash arrow and the non-modulated signal is the solid arrow. The uplink signal received by the dual-frequency antenna goes through the circulator and the high-pass filter.

The smaller signal derived from the 10 dB coupler is doubled by a frequency doubler (FD) 63, and then adaptively manipulated by the tunable attenuator (ATT) 64 and phase shifter (PS) 65 to tune the signal added to the received NCS-modulated signal by the combiner (CB) 66. The combined signal then goes through the Rx chain of the SDR. In the depicted embodiment, the circuit modules from the CPL 62 of the Tx side to the CB 66 at the Rx side make up the cancellation network, which will increase the Rx dynamic range from matching the NCS-modulated and non-modulating signals. Based on the received signal from SDR, the feedback control loop for ATT 64 and PS 65 is established, where the Rx gain can be further boosted to amplify the NCS-modulated vital-sign signal to reveal the signal details from heart sound. In an experimental embodiment, at least another 10 dB gain at the Rx chain could be added. The cancellation network shown is intended to be illustrative, and other configurations of cancellation networks may be used. For example, the cancellation network can also be used to compensate for interference caused by body motion (for example, whole body motion) and other sources with more sophisticated signal processing, such as the pilot tone signal injection in Tx to analyze the received signal and to manipulate ATT and PS accordingly.

Experimental Results

Figure 20:
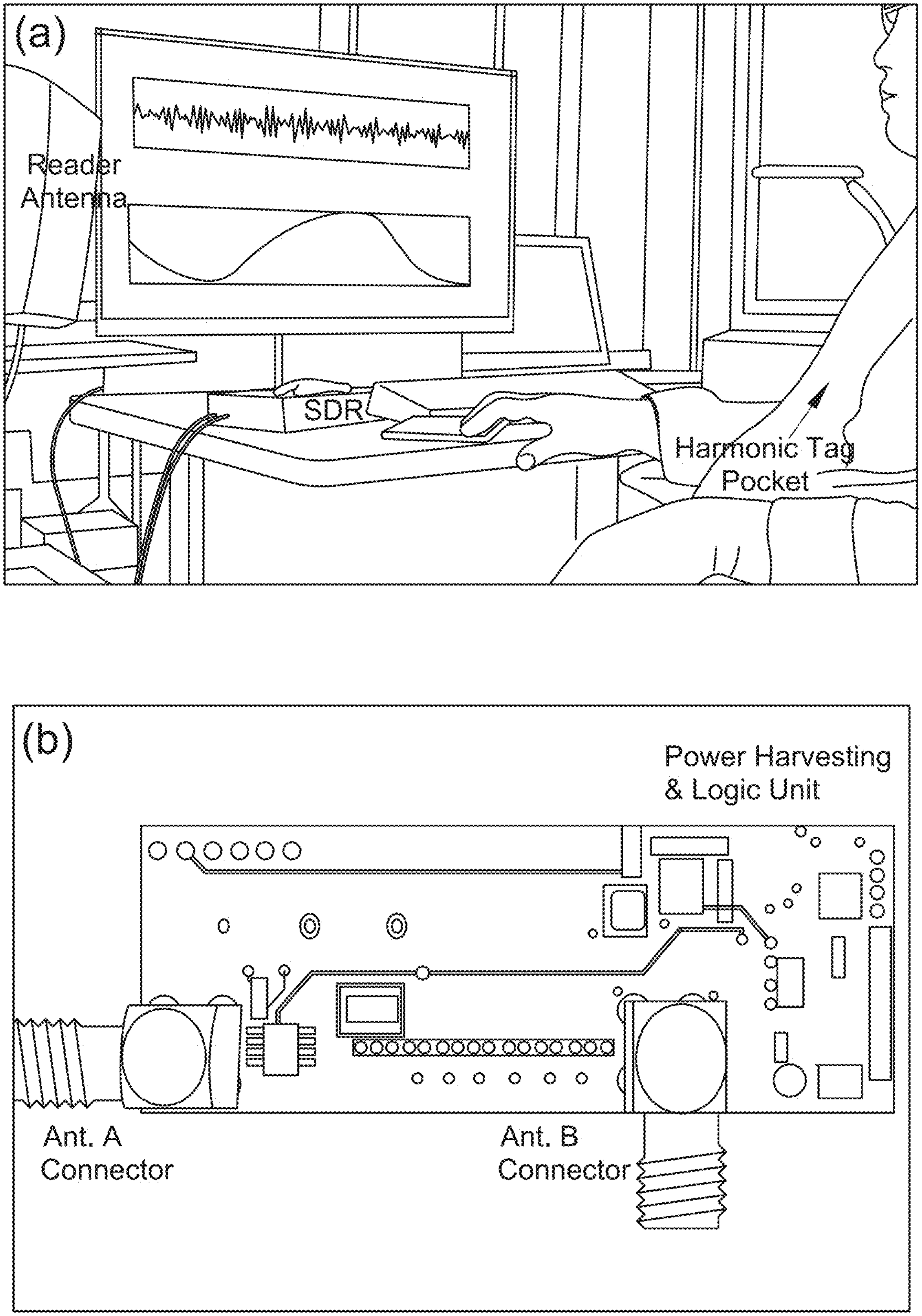
FIG. 20. (a) An experimental NCS setup with passive RFID tag in the front pocket on the chest area. (b) The harmonic tag used in (a).

An experimental NCS measurement system for heart measurement was setup and is shown in FIG. 20. A harmonic tag was placed into the front pocket of a test subject at the chest area. An SDR by Ettus B210 was connected to a computer through its USB port, and the RF ports were connected to the cancellation network, circulator, and a dual-band reader antenna. Vital-sign signals were demodulated by the SDR and computer as shown on the screen.

Figure 21:
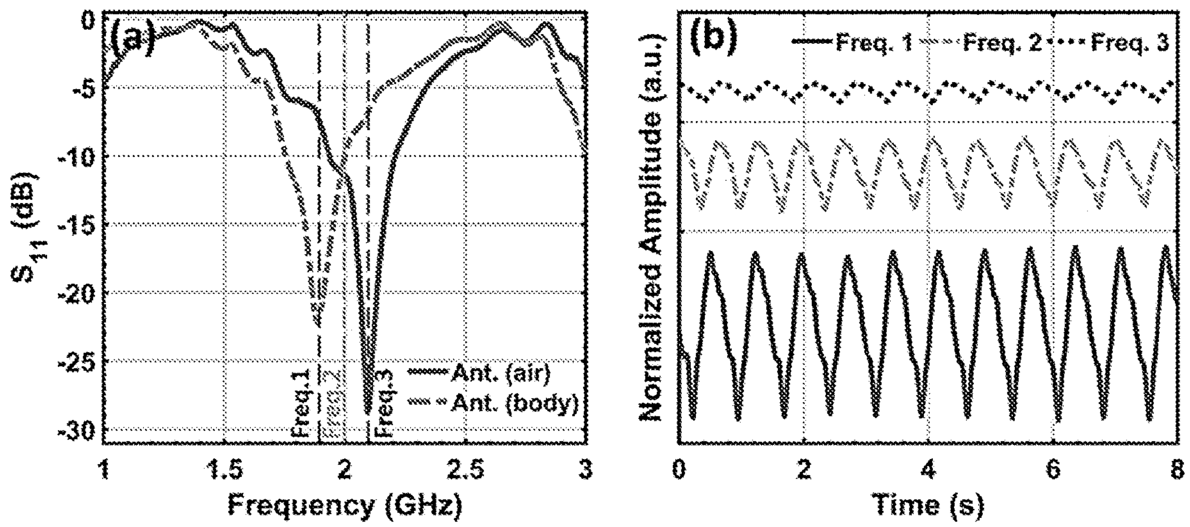
FIG. 21. Experimental results in various frequencies. (a) $S_{11}$ of the NCS antenna when it is operated in air (solid curve), and placed on the chest (dashed curve). (b) The heartbeat signal waveforms demodulated from the chest tag in FIG. 20 with different sensing frequencies. The NCS signals from the solid curve (impedance matched condition), the dashed curve, and the dotted curve correspond to Freq. 1,2, and 3 in FIG. 21(*a*), respectively.

A monopole antenna was used as the sensing antenna for the experimental NCS setup. The $S_{11}$ of the antenna is shown in FIG. 21(*a*). The solid line with the center frequency of 2.1 GHz represents operation in free space. For placement near the chest area, the antenna $S_{11}$ response shifts to the dashed line with the center frequency at 1.9 GHz. The reflection around 2.1 GHz is now much higher. To achieve large energy coupling and high signal-to-noise reduction (SNR) in NCS, the downlink signal may be changed to, for example, 950 MHz so that the sensing antenna is well matched at 1.9 GHz. As shown in FIG. 21(*b*), the solid line is the heartbeat signal acquired by the uplink at 1.9 GHz (corresponding to Freq. 1 in FIG. 21(*a*)). The dashed line with the uplink at 2.0 GHz (Freq. 2 in FIG. 21(*a*)) and the dotted line at 2.1 GHz (Freq. 3 in FIG. 21(*a*)) have much weaker NCS signals due to less energy coupling inside the torso. It was noted that the RF radiation efficiencies at Freq. 2 and Freq. 3 were still reasonably high, estimated at 90% and 80% at $S_{11}$ of −10 dB and −7 dB, respectively. Therefore, most of the degradation in the NCS signal can be attributed to the reduction in the tissue coupling. All measurements were conducted under the same setting and extraction procedure except for the different frequencies.

Figure 22:
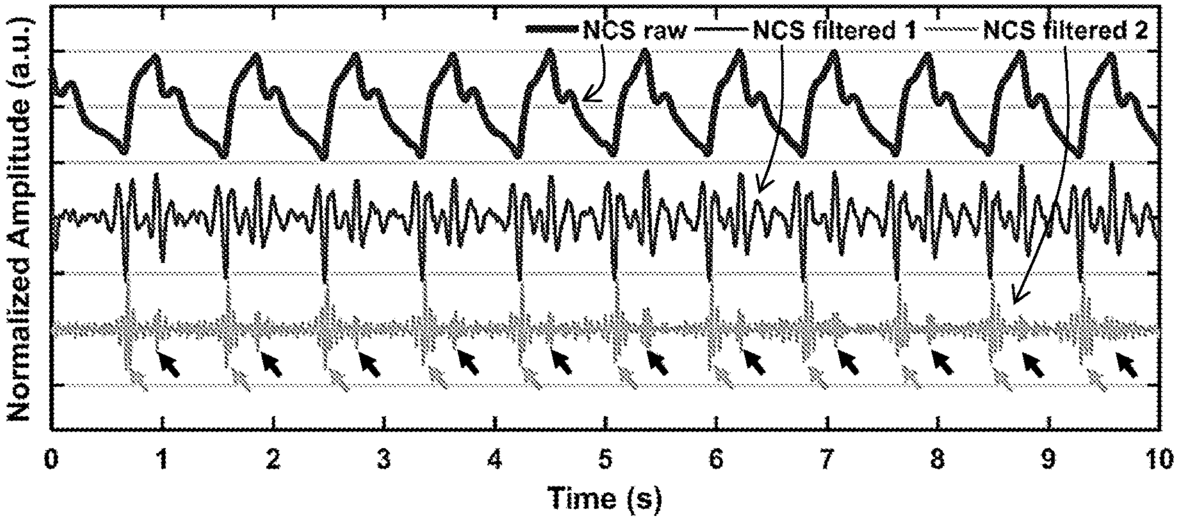
FIG. 22. Graphs showing experimental extraction of the heartbeat waveforms from NCS. Bandpass filter 1 of 6-58 Hz shows high-frequency features without the fundamental heartbeat; Bandpass filter 2 of 16-58 Hz shows the S1 (gray arrows) and S2 (black arrows) locations.

With operation at a frequency providing antenna impedance matching (950 MHz for downlink and 1.9 GHz for uplink), the ATT and the PS in the cancellation network could be tuned to achieve higher Rx gain. The received heartbeat signal waveforms are shown in FIG. 22. The top curve is the NCS heartbeat raw data. Because the NCS signal is related to the mechanical motion of the dielectric boundaries, the strong fundamental heartbeat signal is dominating. However, using the presently-disclosed system design, the weaker high-frequency signal could still be amplified and captured within the ADC resolution. The middle curve of FIG. 22 is the NCS heartbeat signal after a 6-58 Hz bandpass filter was applied. The repeatable details now reveal more heartbeat features. The bottom curve of FIG. 22 shows the signal after a 16-58 Hz bandpass filter where the timing of S1 (gray arrows) and S2 (black arrows) in the cardiogram can be clearly observed. The filtered signal was fed to a speaker, and the S1 and S2 features (caused by the closure of the atrioventricular (AV) valves and semilunar (SL) valves respectively) were clearly audible.

Figure 23:
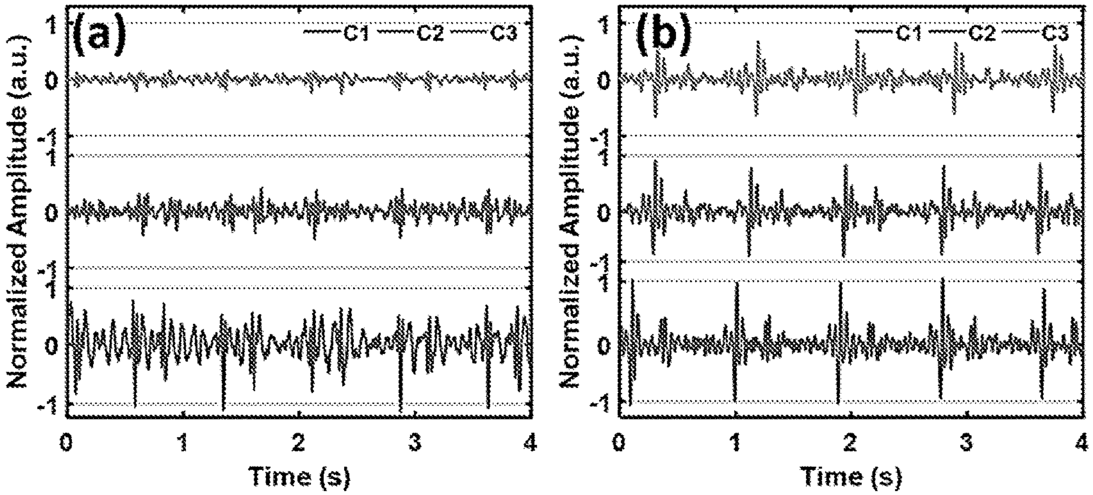
FIG. 23. Graphs showing heart sound waveforms with layers of clothes. (a) The stethoscope recordings: C1 for direct skin contact; C2 for outside a shirt and a sweater; C3: for additional coat. Signals are severely degraded due to acoustic impedance mismatch. (b) The wave-forms from NCS recordings: C1 for outside the shirt without direct skin contact. C2 and C3 are the same conditions as (a).

FIG. 23 illustrates advantages of the present NCS system for operations over layers of clothing. Due to acoustic impedance mismatch and damping, the stethoscope recording deteriorates severely in FIG. 23(*a*) even when appropriate pressure was applied, while NCS maintains the waveform features with slight decrease in magnitude in FIG. 23(*b*) over shirt, sweater, and coat.

Heart Sound Analyses

Figure 24:
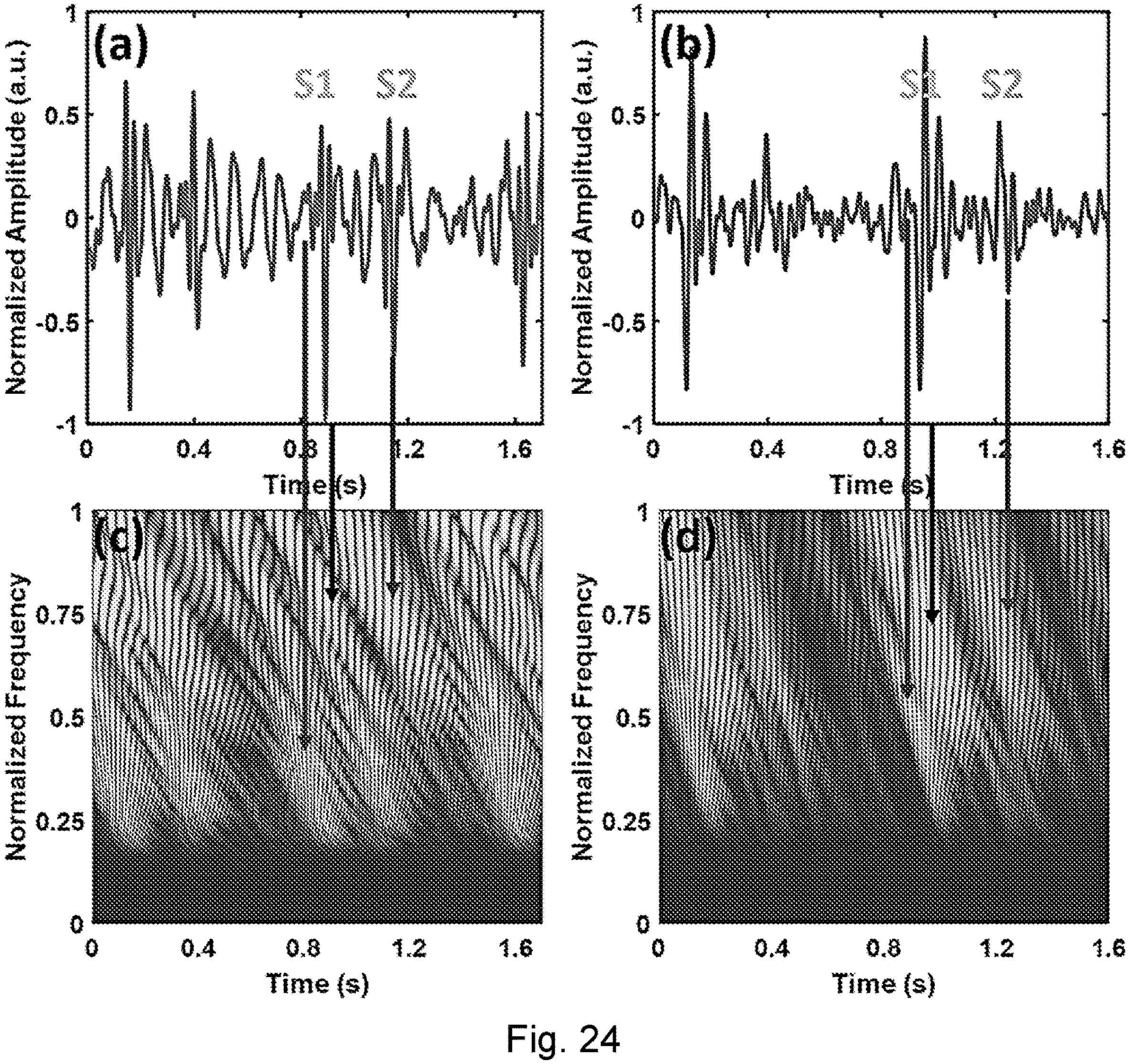
FIG. 24. Heart sound analyses from a single user. (a) The heart sound waveform recorded by the acoustic stethoscope. (b) The heart sound waveform processed from the NCS system. (c) The continuous wavelet transform (CWT) time-frequency analysis of (a). (d) The CWT analyses of (b). The left, middle, and right arrows indicate the similar frequency components of stethoscope and NCS signals.
Figure 25:
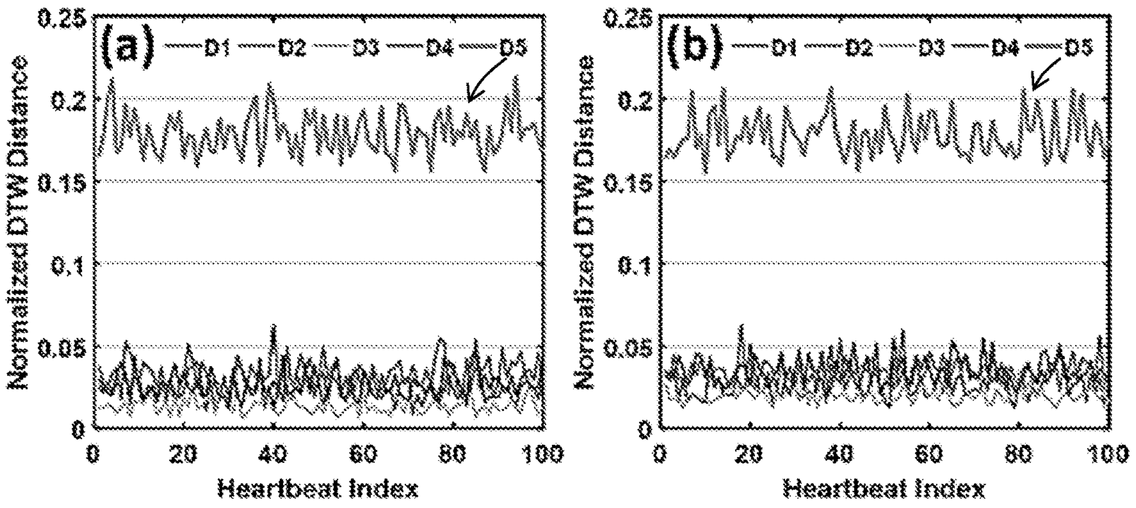
FIG. 25. Heart sound analyses from a single user. (a) The normalized DTW distance of S1 waveforms. D1: between the S1 wave-form and that of the next heartbeat from stethoscope. D2: between two recordings from stethoscope. D3: between the S1 waveform and that of the next heartbeat from NCS. D4: between two wave-forms from NCS. The distance is normalized to the distant value between the averaged NCS S1 waveform and the zero-amplitude signal. D5: between two waveforms from stethoscope and NCS. (b) Similar analyses as (a) but for S2 waveforms.

For heart-sound recordings to be used for diagnostic and biometric purposes, the signal consistency was validated for one individual at different time instances, and sufficient distance between two users. Sample waveforms from the acoustic stethoscope and the experimental NCS system are shown in FIG. 24, which have the same AV and SL valve origins but different transducing paths. The transient waveforms in FIGS. 24(*a, b*) can be potentially matched by spectral equalization, but such practice will be specific to each user and thus less useful. To compare the experimental NCS heart sound system to the acoustic stethoscope, we first show the wavelet analyses in FIG. 24(*c, d*), which illustrates the related heart-sound content with similar time-frequency patterns. NCS has more distinctive features than the acoustic stethoscope possibly due to the more concentrated coupling regions around the heart, and the acoustic stethoscope can contain other sounds from the torso and the ambient even though the recording was done with the individual was holding their breath. We then used a dynamic time warping (DTW) method commonly used in voice recognition for waveform comparisons. The D1-D4 curves in FIG. 25(*a*) show the S1 signal self-consistency in both acoustic stethoscope and NCS by the comparison with the next heartbeat and between two instances of recordings. The DTW distance is normalized by the signal distance to the null vector. The D5 curve shows the DTW distance between the stethoscope and NCS. Despite different transducing paths, the normalized distance was still small around 0.18 as the two signals were correlated to the same sound source. The same trend can be observed for the S2 signal in FIG. 25(*b*).

Figure 26:
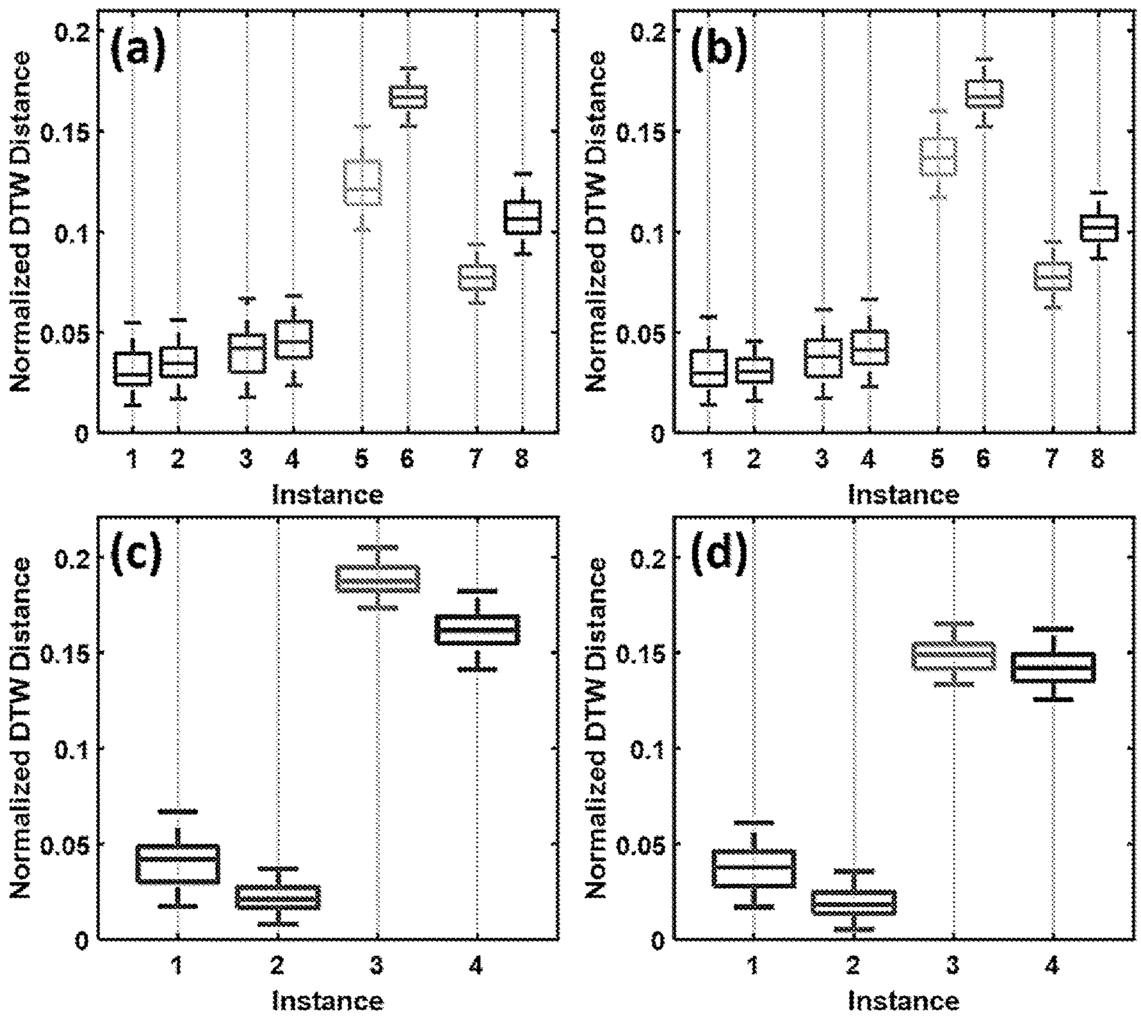
FIG. 26. Normalized DTW distance for heart sound to illustrate the effects from different users and NCS designs. (a) S1 analysis for one user. Instance 1: between the first array of S1 waveforms (Array 1) and their own averaged waveform from stethoscope. Instance 2: between the second array of S1 waveforms (Array 2) and the averaged waveform of Array 1 from stethoscope. Instances 3 and 4 are the comparable data sets from the NCS signals. Instance 5: between the stethoscope S1 waveforms and the NCS averaged 51 waveform. Instance 6: between the NCS S1 waveforms and the stethoscope averaged S1 waveform. Instance 7: between the NCS S1 waveforms at 2.0 GHz and the NCS averaged waveform template in Instance 3 at 1.9 GHz. Instance 8: between the NCS S1 waveforms at 2.1 GHz and the NCS averaged waveform template in Instance 3 at 1.9 GHz. (b) Similar analyses as (a) but for S2 waveforms of one user. (c) NCS S1 analyses for two users. Instance 1: between User 1 (male) waveforms and his own averaged template. Instance 2: between User 2 (female) and her own averaged template. Instance 3: between User 2 waveforms and the averaged template from User 1. Instance 4: between User 1 waveforms and the averaged template from User 2. (d) Similar analyses as (c) but for S2 waveforms.

In FIG. 26, the normalized DTW distance is used to illustrate the effects from different users and NCS system designs. For one user, the signal self-consistency from the acoustic stethoscope and NCS can be established from the very small distance in Instances 1-4 for S1 and S2 in FIGS. 26(*a*) and (*b*), respectively. Instances 5 and 6 show the distance between acoustic stethoscope and NCS, which is similar to the analysis in FIG. 25. Instances 7 and 8 illustrate the signal degradation effect when the NCS antenna is not operated at the impedance-matching frequency, where larger distance would be observed for less signal consistency. Finally, in FIGS. 26(*c*) and (*d*), two users with their own NCS signal self-consistency (Instances 1 and 2) have much larger distance (Instances 3 and 4) in both S1 and S2 waveforms.

MIMO Heart Measurement Experimental Embodiments and Discussion

Figure 9:
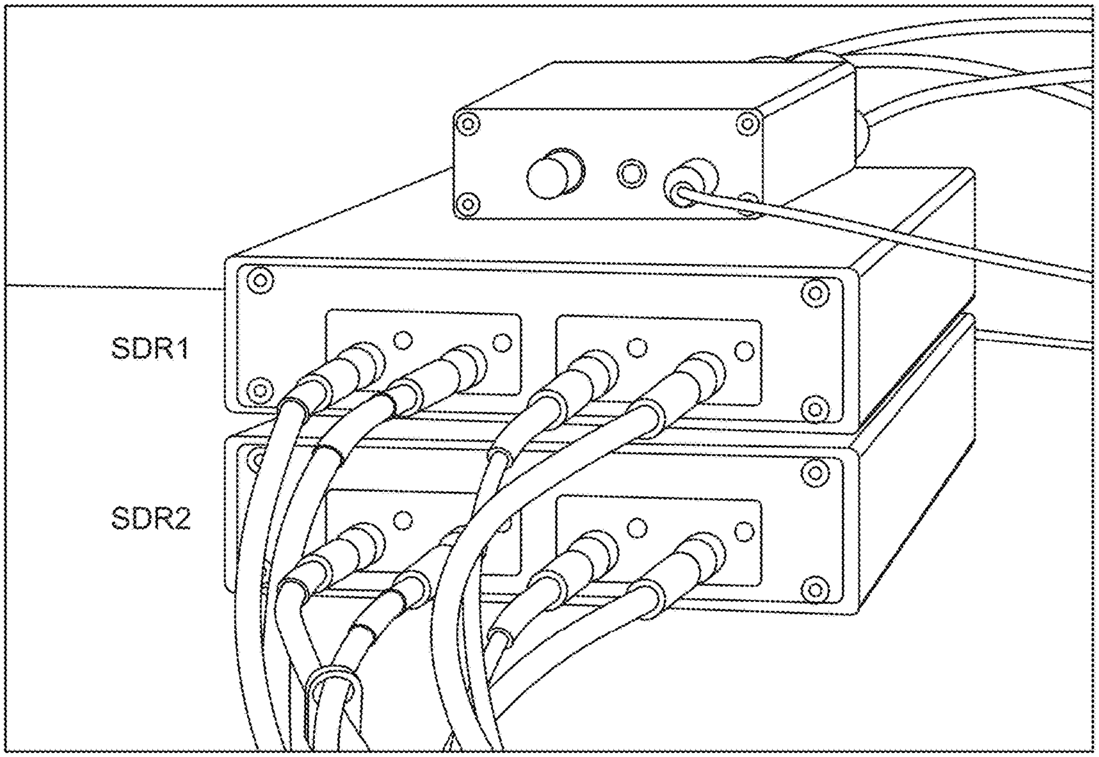
FIG. 9. A photo of an exemplary MIMO NCS system using two coherent software-defined radios (SDR, Ettus USRP B210).

In some embodiments, the present disclosure provides a multi-static, MIMO NCS system, an exemplary embodiment of which is shown in FIG. 4(*a*). The use of multiple observation channels in this way is helpful in resolving complex heartbeat dynamics (though this is not to be limiting and embodiments can be used to resolve other complex motion dynamics). The experimental embodiment of FIG. 4(*a*) was constructed using two software defined radios (SDR), denoted as SDR1 and SDR2. The two SDRs were synchronized by an external local oscillator (LO) with a 10 MHz reference and 1 PPS (pulse per second) baseband synchronization. A picture of the fully coherent system is shown in FIG. 9. It should be noted, however, that the system may be embodied using other configurations (for example, multiple SDRs each having one transceiver, etc.)

A first RF sensing signal is provided at a first location within a near-field coupling range of the heart motion. In this way, a first measurement signal is generated. The method includes detecting the first measurement signal at the first location and measuring the first motion based on the first measurement signal. A second RF sensing signal is provided at a second location within a near-field coupling range of the heart motion. In this way, a second measurement signal is generated. The method includes detecting the second measurement signal at the second location and measuring the second motion based on the second measurement signal.

More than two locations may be used. As such, a method for measuring heart dynamics may include providing two or more RF sensing signals each at a location which is different than the others. In this way, corresponding measurement signals are generated (the two or more sensing signals modulated by the heart at their respective locations). Each measurement signal is detected at its corresponding location and cross channels. The heart motion is measured based on each measurement signal.

For example, each sensing signal may be ID-modulated (having a unique digital identification modulated onto the signal). The sensing signals may be active radio links or backscattered RFID links. Each sensing signal may be provided by a wireless tag, such as an RFID tag. Such tags may be wearable. For example, the tags may have adhesive to be affixed to, for example, the individual's skin. In some embodiments, the tags may be configured to be affixed to or sewn into the individual's garment. The method may further include providing downlink signals to power the wireless tags. The sensing signals may be at frequencies which are each a harmonic of the corresponding downlink signal.

In a particular embodiment used to illustrate the presently-disclosed techniques (and in experimental embodiments further described below), the method may include providing four or more RF sensing signals. A first RF sensing signal is provided proximate to an aortic valve of the heart. A second RF sensing signal is provided proximate to a mitral valve of the heart. A third RF sensing signal is provided proximate to a pulmonary valve of the heart. A fourth RF sensing signal is provided proximate to a tricuspid valve of the heart. The method includes detecting four measurement signals corresponding to the sensing signals, and may include detecting cross-coupled measurement signals.

Each port of the exemplary NCS system includes one RF transmitter (Tx) and one receiver (Rx). In Port 1 (Po1), a field-programmable gate array (FPGA) prepares a baseband signal to be fed to the Tx chain (blue triangle), where the Tx end of the first NCS sensing antenna pair (shown in FIG. 10) is connected to Tx1 and the Rx end to Rx1 (red triangle) in SDR1. The received RF signal modulated by the heartbeat is fed to Rx1 and demodulated by FPGA. The other three ports (Po2 to Po4) are similarly configured with Tx2 and Rx2 to Po2 in SDR1, Tx3 and Rx3 to Po3 in SDR2, and Tx4 and Rx4 to Po4 in SDR2. Each antenna pair is deployed at a designated sensing point to realize multiple observation channels. The MIMO RF signal can be multiplexed with time-division multiple access (TDMA), code division multiple access (CDMA), or frequency division multiple access (FDMA). FDMA was used in the non-limiting, experimental embodiment described herein. The carrier frequency in the demonstration was 1.82 GHz with 0.71 MHz, 1.22 MHz, 1.71 MHz, and 2.33 MHz offsets for Tx1-Tx4, respectively. Other frequency choices are also possible as long as the heartbeat is within the near-field range of each antenna. The four sensing antenna pairs were placed at the positions shown at Points 1-4 in FIG. 4(*b*) accordingly (a photo is shown in FIG. 11). The positions of Points 1-4 were chosen by mimicking a conventional auscultatory stethoscope to listen to the aortic, mitral, pulmonary, and tricuspid valves. Point 0 was set to a central area as a reference position in the experiment of timing comparison. For the full MIMO capability in the four-port system, the dual-SDR system can be configured to implement cross-port channels as well, such as Tx1 to be received by one or all of Rx2, Rx3, and Rx4. An electrocardiogram (ECG) recorder was also deployed. In FIG. 4(*b*), LL denotes the left leg electrode, and RA denotes the right arm electrode, both of which were pasted on the torso as shown in the figure. The ECG signal was used as a timing reference for MIMO NCS to highlight the feature points in the cardiac cycle. A synchronized digital stethoscope recorded the S1 and S2 heart sounds at the auscultation Point ST in FIG. 4(*b*). The ECG electrodes and the stethoscope drum require direct skin contact to acquire clear signals, but the NCS sensing antennas can be put outside the clothing due to the effective RF penetration in the UHF band. All NCS, ECG, and stethoscope recordings were synchronized in the host computer.

Synchronized ECG

Figure 5:
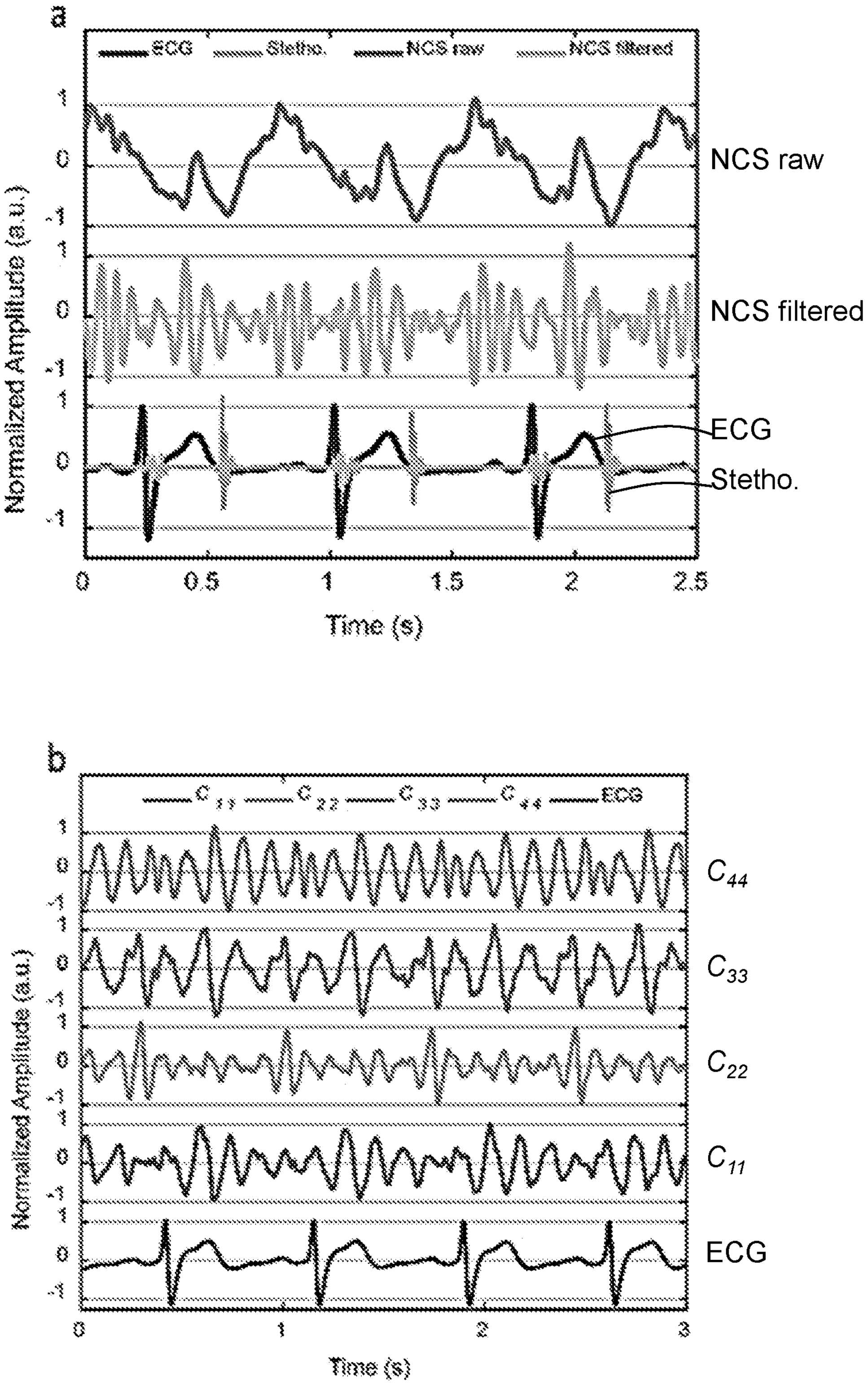
FIG. 5. Comparison of synchronized NCS, ECG, and stethoscope waveforms. (a) A single-channel NCS at Point 0 is labeled “NCS raw,” a high-frequency NCS waveform after bandpass filtering of 7-20 Hz is labeled “NCS filtered,” and ECG and stethoscope signals are shown. (b) Synchronized MIMO NCS backscattering channels. The waveforms from $C_{11}$ to $C_{44}$ are from Points 1-4 in FIG. 4(*b*), respectively. A synchronized ECG curve is shown for timing reference. (c) Cross-port (cross-coupled) NCS waveforms $C_{21}$, $C_{12}$, $C_{43}$ and $C_{34}$ are Tx1 to Rx2, Tx2 to Rx1, Tx3 to Rx4, and Tx4 to Rx3. A synchronized ECG serves as a timing reference.
Figure 5:
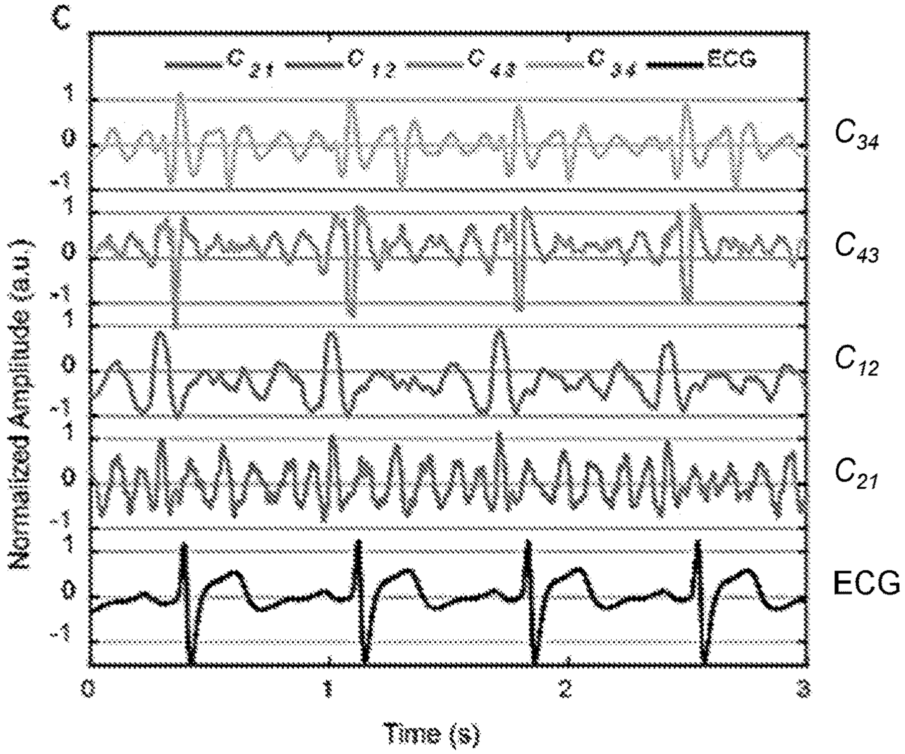

The timing relation among the synchronized ECG, stethoscope, and single-channel NCS signals is shown in FIG. 5(*a*), where the NCS antenna pair is located at Point 0 (Erb's point) in FIG. 4(*b*). The demodulated NCS raw recording is shown, as well as its zero-phase bandpass filtered (7-20 Hz) waveform to highlight the high-frequency components. The synchronized ECG and stethoscope waveforms are also shown. The first heart sound (S1) happens around the R-S period of the ECG caused by the closure turbulence of the atrioventricular (AV) valves, and the second heart sound (S2) is at the end of the T wave generated by that of the semilunar (SL) valves. These timing features will be aligned in the physiological Wiggers Diagram in later analyses (described below).

Figure 12:
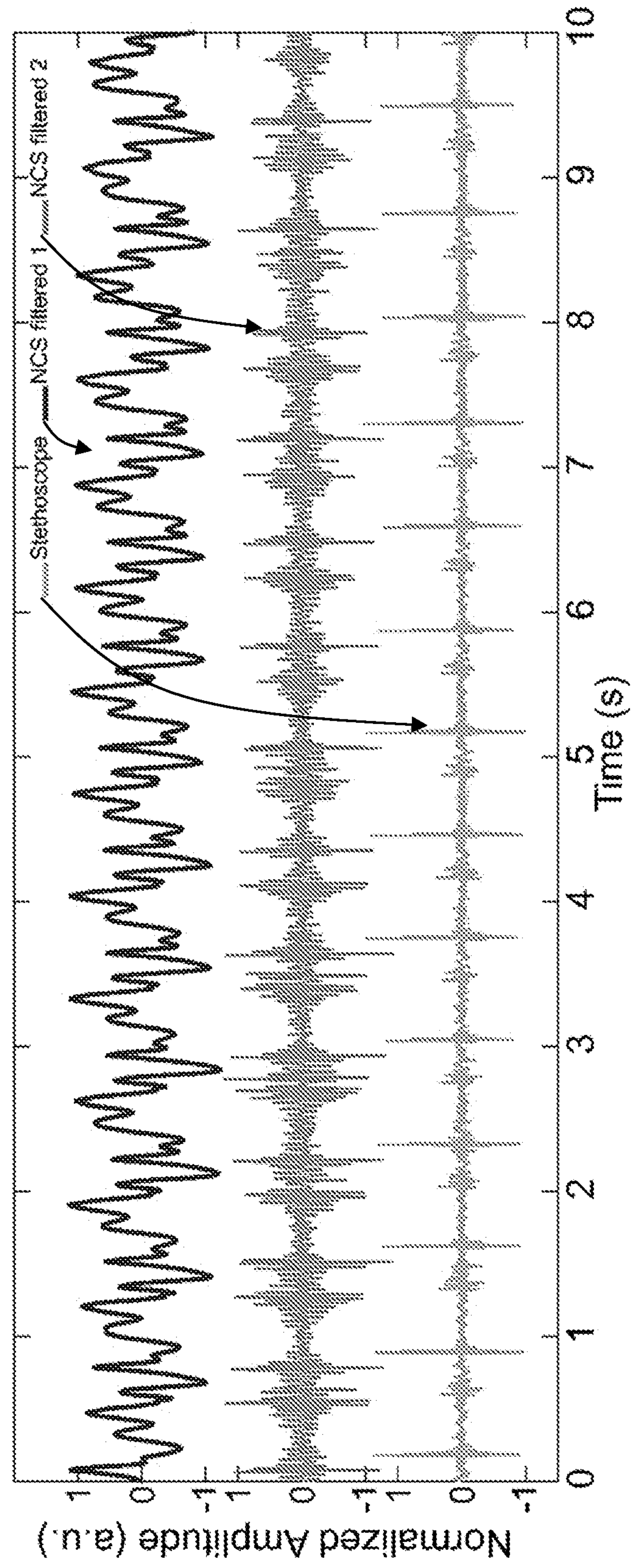
FIG. 12. A trace showing audible-frequency components filtered from an exemplary NCS signal in comparison with a synchronized stethoscope signal.

As the NCS signal is modulated by the mechanical motion of the dielectric boundaries in its signal path, the received NCS raw waveform is dominated by the strong fundamental tone. Additionally, the details of the internal motion of the atria, ventricles, valves, and artery are also coupled to the NCS signal and each motion has its frequency features and timing. Similar to the audible sound analysis, the higher frequency component will show lower amplitude for the same energy spectrum. The high-frequency information of the heartbeat is thus visually overwhelmed by the low-frequency component in the time domain. After bandpass filtering was applied to the raw NCS signal, the high-frequency features can be more clearly viewed in the systole and diastole phases. However, some NCS features are not included in either ECG or stethoscope. ECG measures the electrical activity started from the sinoatrial node, which does not carry the direct information of the mechanical motion. Stethoscope on the other hand can only capture vibration in the audible range determined by the acoustic impedance matching of the applicator, and will likely miss the low-frequency information. From FIG. 5(*a*), we can clearly observe that no clear stethoscope signal is present between S1 and S2, but the bandpass-filtered NCS signal still contains many features, which are likely to be derived from the atrial and ventricular chambers with motion characteristics that cannot be picked up by the stethoscope. On the other hand, when appropriate bandpass filtering (16-120 Hz) is applied, the NCS signal can show most of the information in the acoustic stethoscope, as illustrated in the FIG. 12.

With regard to the experimental four-port MIMO NCS system synchronized to an electrocardiogram (ECG), the four NCS sensing antenna pairs may be placed at Points 1-4 in FIG. 4(*b*), respectively. FIG. 5(*b*) shows the channels of Tx1-to-Rx1 (Cu), Tx2-to-Rx2 ($C_{22}$), Tx3-to-Rx3 ($C_{33}$) and Tx4-to-Rx4 ($C_{44}$) after the same zero-phase bandpass filtering (7-20 Hz). The synchronized ECG in the bottom curve is shown for timing reference. The system setups of the four backscattering channels are the same, but each sensing antenna pair may have its own weighted coupling to the different parts of the heartbeat. $C_{11}$ and $C_{33}$ have stronger signals just after the QRS complex when the heart ejects the blood from the ventricles to the artery through the SL valves. Analogous to the auscultation position, CH will have more emphasis on the aortic valve and artery, while $C_{33}$ more on the pulmonary valve and artery. Similarly, $C_{22}$ contains more mitral valve motion during the P-R period, and $C_{44}$ more tricuspid valve information although it would also couple in the strong left ventricular motion during the T wave. The aortic cycle usually has larger motion and higher pressure than the pulmonary cycle due to the higher vascular resistance.

Figure 13:
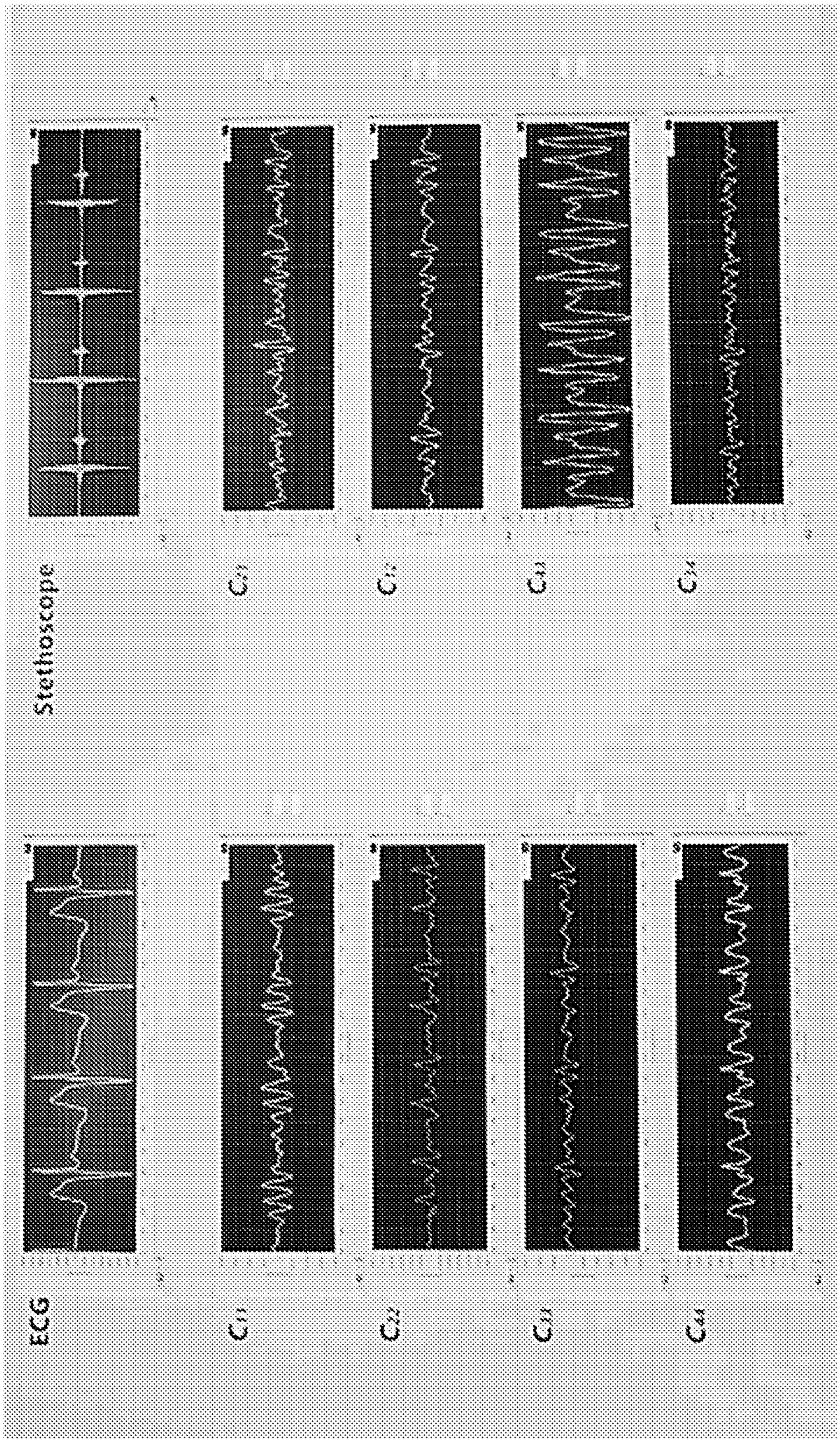
FIG. 13. A sample display showing eight coherent channels in MIMO NCS, as well as synchronized ECG and stethoscope waveforms.
Figure 14:
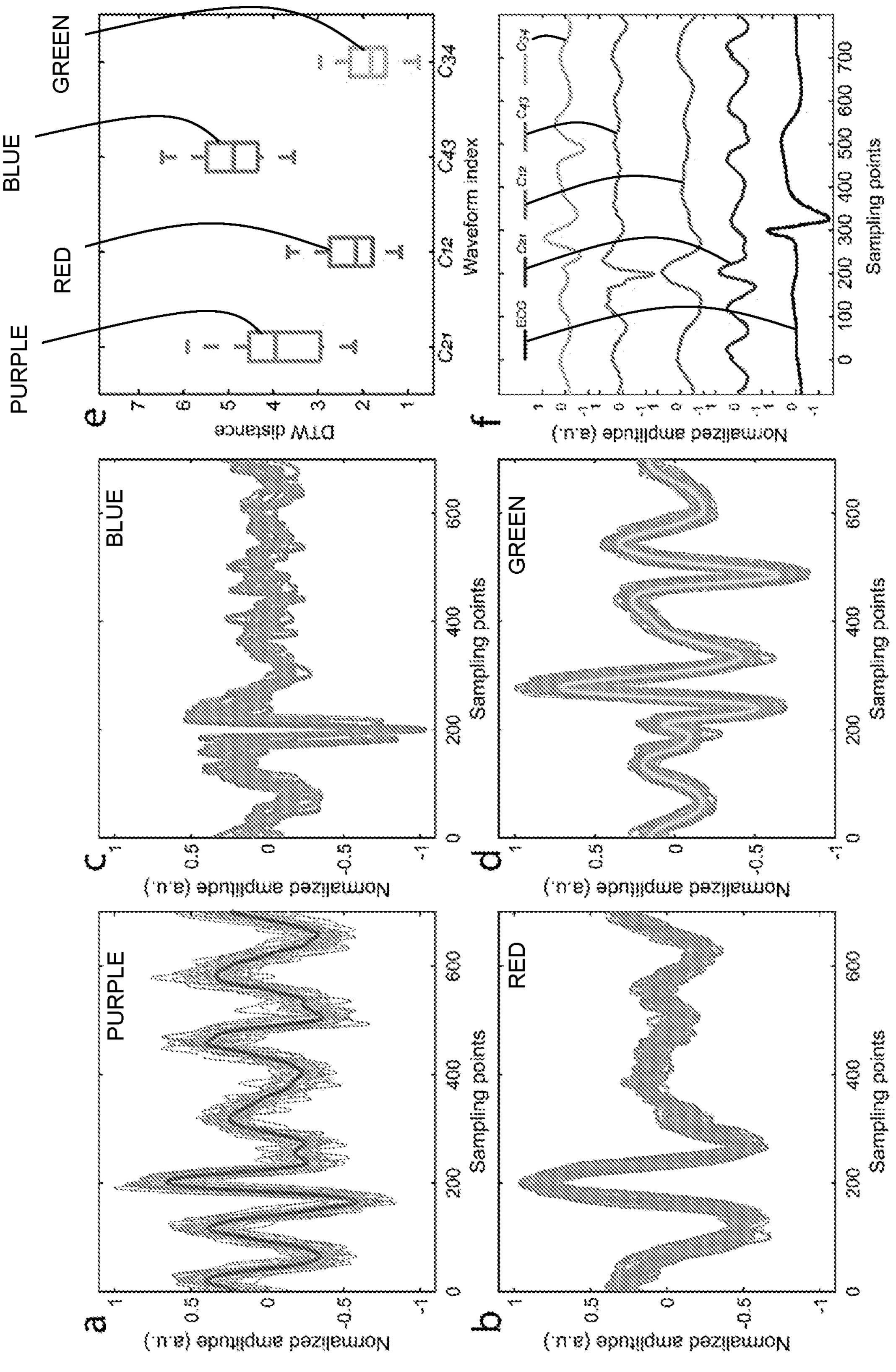
FIG. 14. Graphs showing waveform analyses by dynamic time warping (DTW) for 300 heartbeats of a first person observed from NCS cross-port channels: (a) $C_{21}$; (b) $C_{12}$; (c) $C_{43}$; (d) $C_{34}$. The purple, red, blue, and green curves are the averaged waveforms to serve as the template. Other waveforms of the same channel are overlaid as gray curves. (e) The DTW distances against the corresponding template waveforms. (f) The $C_{21}$ to $C_{34}$ waveform templates in comparison with ECG.

The MIMO NCS system can observe the heartbeat not only from the different position of each sensing antenna pair with collocated Tx and Rx by backscattering, but also from the multi-static channels. Four cross-port signals are presented in FIG. 5(*c*). For example, the waveform labeled $C_{21}$ is the signal transmitted from Tx1 and received by Rx2. The naming order of Tx-Rx ports follows the convention of the multi-port scattering matrix in microwave component testing. The $C_{12}$, $C_{43}$, and $C_{34}$ curves are the signals from Tx2 to Rx1, Tx3 to Rx4, and Tx4 to Rx3, respectively. The ECG waveform (bottom) remains as timing reference. A plot is shown with descriptions in FIG. 13. Because the collocated backscattering channels are more sensitive to the respective local areas, the purpose of the cross-port observation is to expand the sensing path so that rich content can be collected. Notice that this observation mode is not applicable using a passive stethoscope, but can be an option for ultrasound imaging. Each multi-static channel records a clear cyclic information. After dynamic-time warping (DTW) normalization, the overlaid waveforms from many heartbeats of the same person are shown in FIG. 14. The multi-static waveform results from modulation of the dielectric boundary motion along the cross-port path, which has a nonlinear coupling with stronger weights towards Tx according to the near-field approximation. $C_{21}$ and $C_{12}$ go across the heart region in a longer path and are further away from the strong left ventricle and aortic valve than $C_{43}$ and $C_{34}$. Hence, $C_{21}$ and $C_{12}$ have the largest component during the atrial systole phase around the P-R wave, while $C_{43}$ and $C_{34}$ have larger signals during the isovolumic contraction around the R-S wave. Cross-port waveforms can be further applied to extract the timing and magnitude of the detailed heart dynamics by least-square fitting in the future. More cross-channel analyses of multiple persons are presented in FIGS. 15 and 16.

Blood Pressure Estimation

In some embodiments, the method 100 includes determining 140 a systolic and/or diastolic blood pressure based on the first measurement signal. For example, the method may include determining a pulmonary systolic blood pressure and/or a pulmonary diastolic blood pressure based on the second measurement signal corresponding to the second sensing signal (where the second sensing signal is provided proximate to a mitral valve of the heart).

After illustrating the rich content in MIMO NCS, we will now examine the correlation between the branchial BP measurements and the NCS $C_{11}$ waveform that contains the aortic pressure dynamics during the systole phase. In embodiments of the present NCS, the BP measurement is related to the central BP of the aortic artery instead of the branchial BP given by the arm cuff, although the two values are often reasonably close when the cuff is at the same height of the heart. At the end of the diastole phase, the left and right ventricles of a heart are filled with blood. Then, ventricular contraction is trigged by the QRS signals into the systole phase. FIG. 6(*a*) shows a cross-sectional diagram of a heart ejecting blood from both ventricles into the aorta and pulmonary artery. FIG. 6(*b*) shows the corresponding part of the Wiggers Diagram for the timing relation between ECG and the aortic pressure. The systole period is between the black dashed lines, where the tricuspid and the mitral valves are closed to inhibit regurgitation and thus the atria have negligible motion during systole. When the BPs in the ventricles are higher than those in aorta and pulmonary artery, the aortic and pulmonary valves will open, which is indicated by the arrow labeled "aortic valve opens" in FIG. 6(*b*). The ventricular contraction causes the aortic pressure to reach its peak value which is the central systolic BP indicated by the arrow labeled "systolic pressure" around the T wave. Afterwards, the aortic pressure begins to drop due to blood flowed into branchial vessels until the aortic and left ventricle pressures are equal, then the aortic valve closes to form a small cusp in the aortic pressure generating the S2 heart sound, as indicated by the arrow labeled "aortic valve closes." The aortic pressure keeps dropping in the next diastole phase when the AV valves are open for blood to flow from the atria to the ventricles. Immediately after the QRS complex, the aortic pressure reaches the minimum value, which is the central diastolic BP indicated by the arrow labeled "diastolic pressure" where the AV valves close to make the S1 heart sound. As the fluid pressure is positively correlated to the vibration characteristics of the containing viscoelastic vessel and valve, the frequency components in $C_{11}$ would contain the aorta vibration features during systole, and can thus be used to estimate the central systolic and diastolic BP.

Therefore, NCS BP derivation is enhanced by high resolution in both frequency and time. Frequency and time are the Fourier transform pair, and their resolutions are limited by the Uncertainty Principle model. A simple way to observe this limitation is by the short-time Fourier transform (STFT) where a time window is applied to compute the spectrum of an infinite time series. To obtain high time resolution in STFT, the time window length is reduced, which causes the spectrum within the time window to spread out, and thus high frequency resolution cannot be simultaneously achieved. Other methods such as wavelet transform and windowed Fourier transform can mitigate this deficiency to some extent, but the tradeoff between the time and frequency resolutions remains.

To minimize the frequency-time resolution artifact, the Hilbert-Huang transform (HHT) may be used to obtain the frequency-time spectrum. The frequency information is calculated at each sampling time point with the definition of the instantaneous frequency. The time resolution depends on the sampling rate in the time domain, which can be easily above $10^6$ samples per second (Sps) by the analog-to-digital converter (ADC) in the chosen SDR. The high ADC sampling rate can also spread the noise over a larger spectrum to reduce the noise floor and increase the signal-to-noise ratio (SNR). The frequency resolution is chosen for reasonable computation time. CH represents observation from Point 1, which mimics the stethoscope position for the aortic valve murmur. FIG. 6(*c*) is the HHT frequency-time analysis of a single heartbeat obtained from CH when the person under test was seated on the floor. The bottom curve is the synchronized ECG signal to show timing, and the ventricular ejection period is between the dashed lines. The sampling rate for the waveform is $10^3$ Sps with the time resolution at 1 ms. The highest frequency response is half of the sampling rate at 500 Hz. The frequency resolution is set to 0.125 Hz, 1/8000 of the sampling rate.

Figure 17:
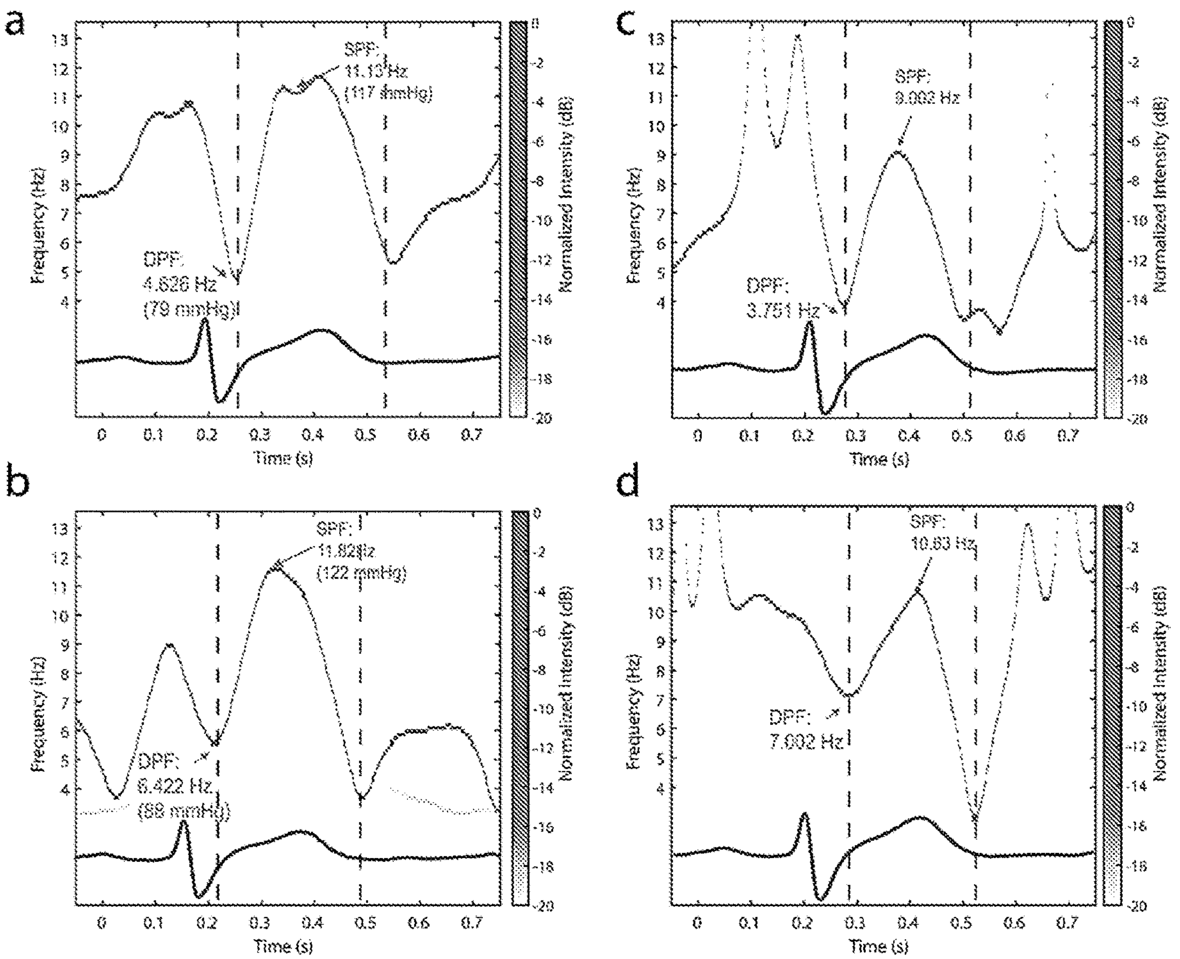
FIG. 17. Graphs showing HHT frequency-time BP analyses of the second person corresponding to FIG. 6. (a) $C_{11}$ HHT when the person sat in the chair. The synchronized ECG signal (lower trace in each chart) indicates the timing and the ventricular ejection period is between the dash lines. (b) $C_{11}$ HHT when the person took a standing posture. (c) $C_{33}$ HHT when the person held breath after maximum exhalation. (d) $C_{33}$ HHT when the person held breath after maximum inhalation.

In FIG. 6(*c*), each colored (shaded) point represents the frequency of the corresponding time and the color (shade) shows the intensity in the dB scale normalized by the respective maximum value. During the ejection phase, the frequency-time points form a red-pink "curve" with a similar shape and timing of the aortic pressure curve in the Wiggers Diagram. The maximum frequency point at 9.427 Hz, denoted as the systolic pressure frequency (SPF), is well aligned with the systolic BP point. The minimum at 4.676 Hz, denoted as the diastolic pressure frequency (DPF), is aligned with the diastolic BP point at the beginning the systole phase. The concurrent BPs measured by an arm cuff monitor (Omron BP760N) are 131 mmHg and 81 mmHg. We then repeated the experiment when the person stood up. The frequency-time analysis is shown in FIG. 6(*d*). The SPF and DPF in this case are 10.88 Hz and 5.126 Hz, and the corresponding arm-cuff BPs are 143 mmHg and 94 mmHg. Two-point linear interpolation can transform the two SPFs to systolic BP, and similarly the two DPFs to diastolic BP in FIGS. 6(*c*) and 6(*d*). The frequency resolution is 0.125 Hz, corresponding to 1.0 mmHg resolution for the systolic BP and 3.6 mmHg for the diastolic BP. The frequency resolution can be further improved by reconfiguring the HHT parameters at the cost of computational time. A measurement from the second person is shown in FIG. 17. Due to the chosen HHT calculation (see Methods below), spurious traces with lower frequency are also observed in FIGS. 6(*c*) and 3*d* by the yellow curves. This ambiguity can be eliminated with the narrower choice of HHT bandwidth or can be simply ignored from its lower magnitude. Notice that the aorta region is the main vibration part in $C_{11}$ HHT only for the systole period. During the diastole phase, there can be other vibration in the vicinity of Point 1 such as the right atrium. However, we do not have a direct method to confirm the physiological meaning of diastole CH at the present time. Analogous to the stethoscope recording, the heart sound S2 originated from the aorta region can be listened from Point 1 over the right atrium which does not have significant vibration during the systole phase. The collected heart sound by SL valve closing is mostly in the frequency range of 16-120 Hz, which is not included in our HHT.

After calibration, we tested the extracted systemic BP in a longer period. The measurements in FIG. 7(*a*) were taken when the person was seated in a chair. The upper and lower curves are the systolic and diastolic BP from 300 continuous heartbeats monitored by $C_{11}$ HHT. The dashed curves are the BP moving averages with a window of 10 heartbeats. The stars are the measurements from the arm-cuff BP monitor. The measurements in FIG. 7(*b*) were taken after the person did some mild exercises and stood up, where the BP relaxation was traced accurately.

Figure 7:
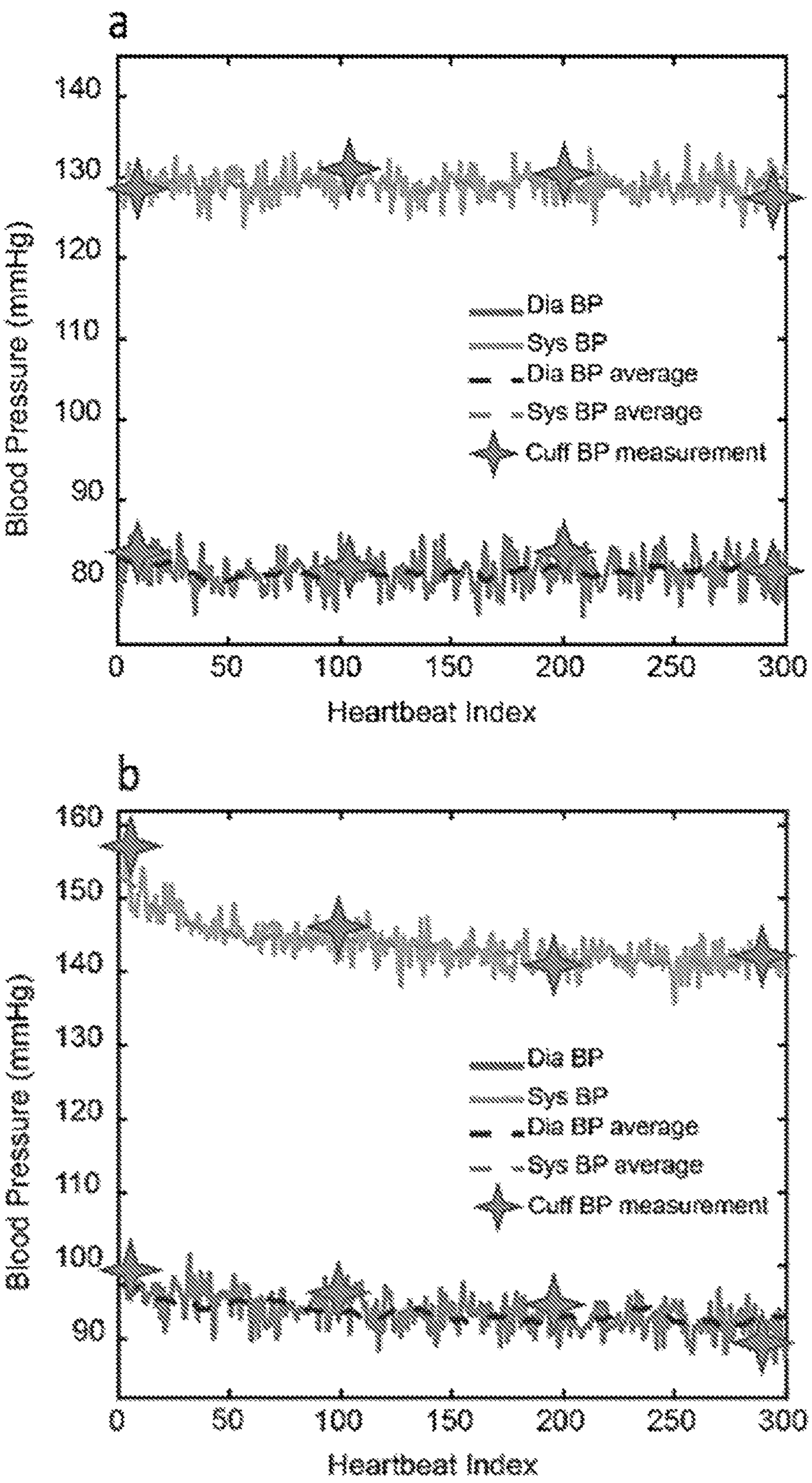
FIG. 7. NCS-derived aortic BP and pulmonary cycle dynamics. (a) The systolic (upper) and diastolic BPs (lower) in the systemic circulation from NCS when the person was seated in a chair. The solid line was evaluated from every heartbeat and the dash line from the moving average of 10 heartbeats. Arm-cuff BP are denoted as stars. (b) Similar analyses to (a) for the person standing after mild exercise. (c) The pulmonary SPF (upper) and DPF (lower). The dark-shaded regions correspond to the person holding their breath after maximal exhalation and the light-shaded regions to holding their breath after maximum inhalation.
Figure 7:
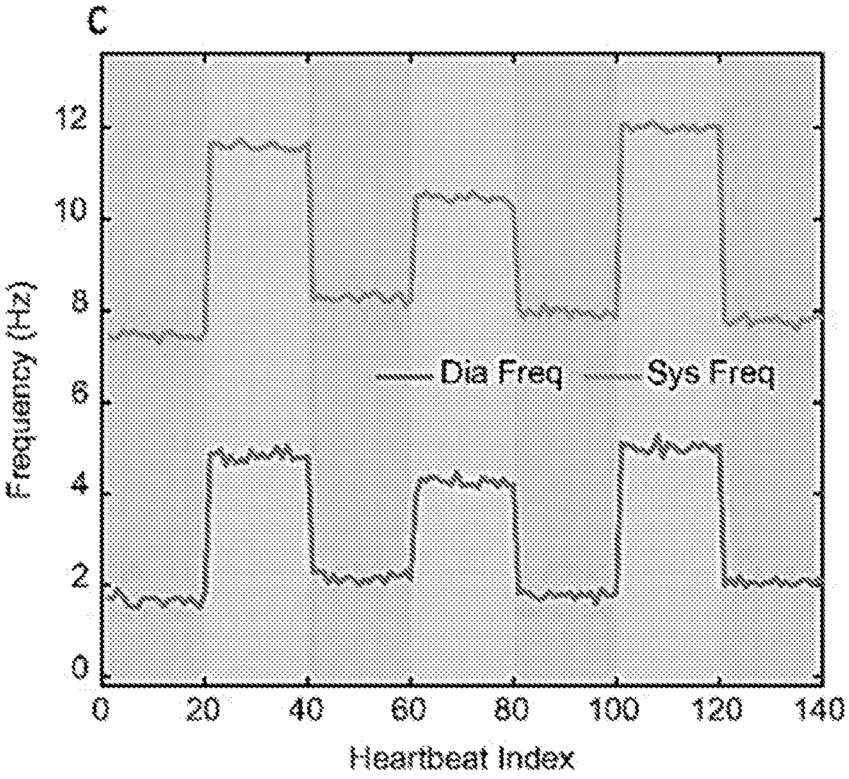

$C_{33}$ at Point 3 in FIG. 4(*b*) corresponds to the auscultatory position to acquire the pulmonary valve murmurs. Similar to the aortic circulation, the pulmonary artery vibration characteristics are related to the right ventricular and pulmonary BP. As the pulmonary BP is more affected by the lung volume due to transpulmonary pressure instead of the posture, FIG. 6(*e*) shows the $C_{33}$ HHT analysis with the synchronized ECG when the person held breath after maximal exhalation. The SPF and DPF were extracted at 7.752 Hz and 1.875 Hz. We then took the measurement in FIG. 6(*f*) when the person held breath after maximal inhalation with SPF and DPF now at 11.38 Hz and 4.376 Hz. Both SPF and DPF increased due to the higher transpulmonary pressure. Lack of access to the cardiac catheterization, the frequencies cannot be quantitatively mapped to BP, but can still be useful to monitor the pulmonary circulation. We analyzed 20 heartbeats for each of the two scenarios and repeated the measurements three times, where the calculated SPF (upper) and DPF (lower) are shown in FIG. 7(*c*).

Discussion

The MIMO NCS system provides a convenient method to acquire rich cardiac dynamics including estimation of the central systemic BP. In comparison with the PTT method which derives both systolic and diastolic BP from one variable, the NCS method can provide SPF and DPF to derive the systolic and diastolic BP independently. SPF and DPF can be calculated from each heartbeat, which cannot be achieved by the arm-cuff monitor. Other approaches analyze the shape of the time-domain waveforms by optical or ultrasound methods to indirectly interpret BP, but are often inconsistent due to the operation variations. Another advantage of the NCS system is the continuous trace of pressure dynamics instead of just two BP points. Although the above description of estimating systemic BP is only derived from $C_{11}$ HHT during the systole phase, the use of multiple channels can provide more reliable parameter extraction for continuous dynamics to all important parts of the heartbeat in the future. As the S1 and S2 heart sounds can be recovered from NCS to provide timing reference, the synchronized ECG is not essential. However, similar to other indirective BP measurement methods, MIMO NCS may benefit from personal calibration to derive BP. BP variation between adjacent heartbeats may result from measurement noises, or may have similar physiological reasons like the heart rate variation.

The critical pulmonary circulation has limited measurement methods previously. The gold standard is the cardiac catheterization, which requires significant setup and highly trained professionals together with considerable risks. Another method is the Doppler echocardiography to derive the pulmonary blood pressure through the velocity of the blood flow. The ultrasound system size is still significant, and the broad-spectrum acoustic impedance matching often demands gel application, disabling wearable fitting or daily usage. The lower sampling rate in Doppler imaging can also reduce its accuracy. On the other hand, NCS can work over clothing and take advantage of the low cost and compact size in modern RF devices such as the smart phone. For various application scenarios, the NCS system can be adapted to the RFID system, wearable devices, and dedicated in-clinic wired setup.

The standard digital filters in the above analyses can be easily realized on various platforms without heavy computational loads. Because HHT is an adaptive algorithm, the computation time depends on the signal complexity and the required resolution. Recent heterogeneous computing design can potentially offer on-line responses.

Methods

A detailed system schematic of a test embodiment is shown in FIG. 18. A 4-port NCS system was built using two SDRs (National Instrument Ettus Research B210). A reference clock signal (BG7TBL-GPSDO) of 10 MHz and 1 PPS was provided to both SDRs by the BNC splitter. The SDRs were connected to a host computer through USB cables. The control software were implemented in LabVIEW. The carrier frequency of the SDR was configured as 1.82 GHz according to the NCS antenna measurements. For each Tx-Rx pair, the baseband frequencies were offset by 0.71 MHz, 1.22 MHz, 1.71 MHz and 2.33 MHz for FDMA. The sampling rates of the ADC and DAC were both set as 5 MSps, which is more than 2 times of the highest baseband offset at 2.33 MHz. After channel demodulation, the NCS signal was down-sampled to 50 kSps as the raw data, which is slightly higher than 44.1 kSps of the reference audio sampling rate so that audible signals can be correctly captured (and utilizing the full capability of the audio channel of the test system). The ECG module (NeuroSky BMD101) was connected to the computer through USB as well, and the digital stethoscope (Thinklabs One) was connected to the microphone port. The NCS, ECG and stethoscope signals were synchronized in LabVIEW. All post processing was performed in MATLAB. For HHT analyses, the 50 kSps raw data were further down-sampled to 1 kSps for computational efficiency. The NCS signal at 1 kSps provides 1 ms time resolution, sufficient to interpret BP for test purposes. A low-pass filter with a cutoff frequency at 200 Hz was applied before down sampling to avoid spectral aliasing. All filters used the zero-phase FIR (finite impulse response) to cancel the phase shift and maintain the linear phase response. The down-sampled signal is further bandpass-filtered (1.5-16 Hz) to diminish the fundamental heartbeat tone and high-frequency heart sound. The signal is then processed by the empirical mode decomposition (EMD) as part of our HHT algorithm, where several intrinsic mode functions (IMF) represent the simple oscillatory modes. The first two IMFs have strong enough intensity to be further processed by the Hilbert spectral analysis (HSA). This procedure can be considered as another filtering which is not based on the pass-stop band, but by the oscillatory modes. Usually the first IMF is much stronger than the second. In FIGS. 6(*e*) and 6(*f*), only one frequency-time curve was observed. In comparison, in FIGS. 6(*c*) and 6(*d*), the spurious yellow curves are caused by the stronger second IMF.

Figure 8:
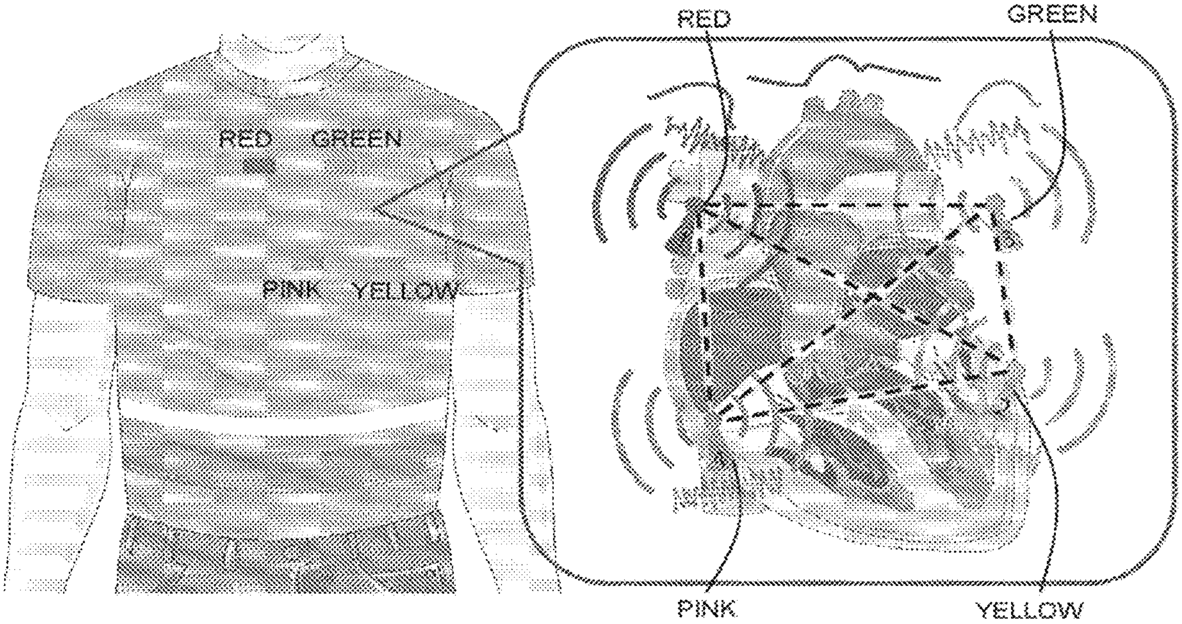
FIG. 8. A diagram of monitoring complex heartbeat dynamics using a wearable radio-frequency MIMO NCS system according to an embodiment of the present disclosure.

Four radio-frequency (RF) antennas as the red, yellow, green and pink (sensing points 1 to 4) blocks are pasted on the shirt around the heart area in FIG. 8. Based on the principle of near-field coherent sensing (NCS) from multiple-input-multiple-output (MIMO) observation, rich content of heartbeat dynamics can be retrieved. The individual sensing antenna interrogates the heartbeat in its vicinity (the wavefront and waveform in the same color of the antenna), and the cross-port signals can also be monitored (the dashed-line paths). The signals from antennas 1 and 3 can be utilized to evaluate the systolic and diastolic blood pressures in both aortic and pulmonary circulations.

The top USRP B210 is labeled as SDR1 in FIG. 9 and the bottom is SDR2. An RF bandpass filter was inserted before each Rx port to improve out-of-band isolation for each channel according to the NCS sensing antenna pair configuration. The top black box is an external local oscillator (BG7TBL-GPSDO) to provide a reference signal of 10 MHz and 1 PPS synchronization to both SDRs. The SDRs were further connected to a host computer running control software in LabVIEW and signal processing algorithms in MATLAB.

Figure 10:
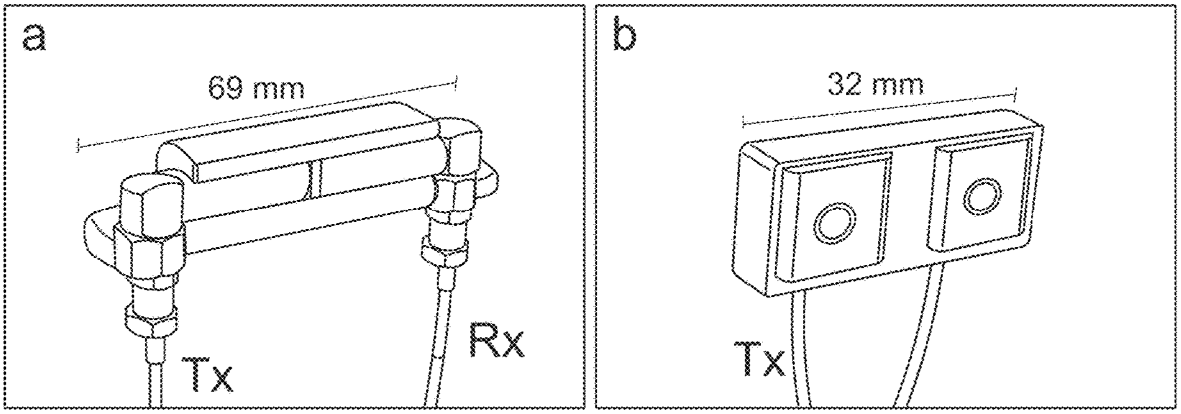
FIG. 10. Photos of an NCS sensing antenna pair: (a) for 1.8 GHz band operation; (b) for the 900 MHz and 5 GHz bands.
Figure 11:
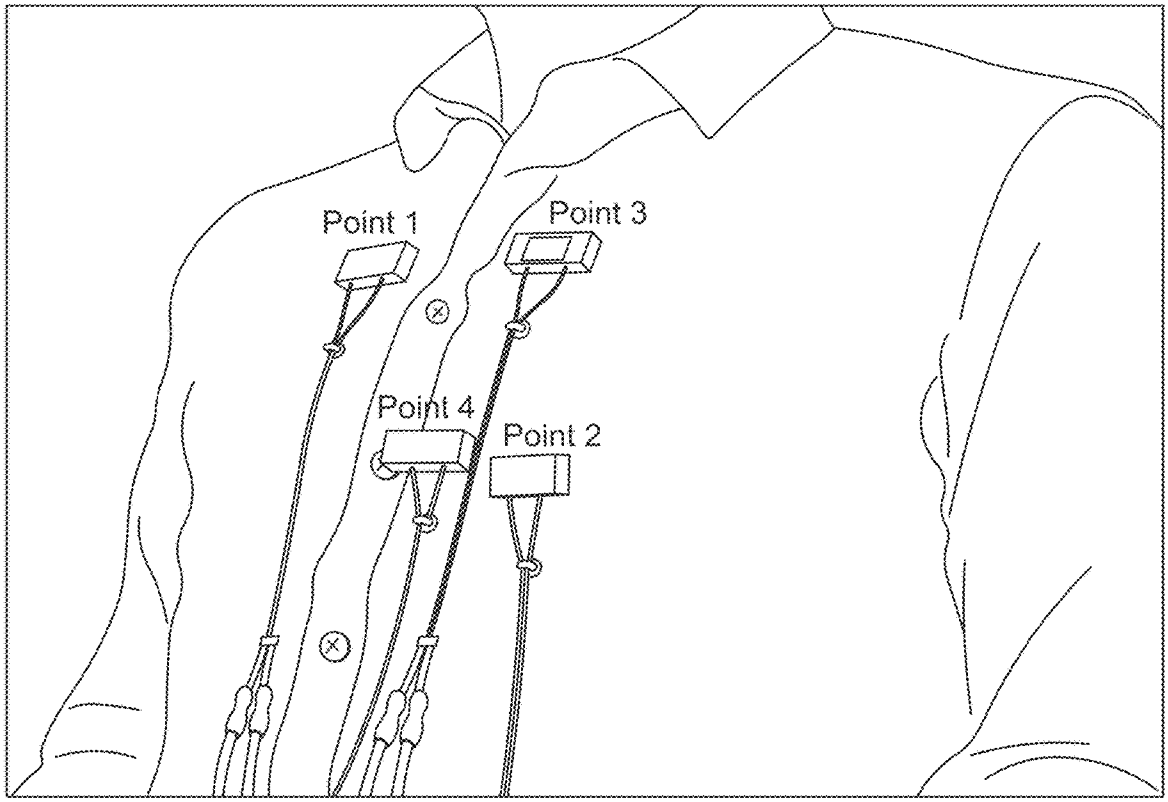
FIG. 11. A photo showing a MIMO NCS sensing antenna placement when four antenna pairs are deployed to Points 1-4 in FIG. 4(*b*).

In FIG. 10(*a*), two monopole antennas (black whips, Taoglas TG.19.0112) are mounted on a 3D-printed holder. The overall dimensions are 69×17×11 mm (W×L×D). The operating frequency is around 1.82 GHz with a bandwidth of 40 MHz. FIG. 10(*b*) shows a smaller NCS sensing antenna pair by two ceramic patch antennas (Taoglas WLP.12C). The overall dimension is reduced to 32×14×5 mm. The operating frequency is around 900 MHz and 5 GHz bands. The operational bands are measured based on the S parameters when the NCS antenna pair is placed on the human chest area (see FIG. 11). The four sensing antenna pairs were pasted on Points 1-4 in FIG. 4(*b*), respectively, by the double-side tapes outside the shirt. Here we used the patch-antenna set in FIG. 10(*b*) with the center frequency at 900 MHz and around 0.21 MHz offset for each channel. The monopole antenna pair was used in other experiments at the 1.82 GHz band.

FIG. 9 shows the NCS signal (from Point 0 in FIG. 4(*b*)) after a high-pass filter with the cutoff frequency of 1.2 Hz (labeled "NCS filtered 1"), and after a band-pass filter of 20-120 Hz (labeled "NCS filtered 2"). The bottom waveform is the synchronized stethoscope recording.

During the data collection, the person under test had no intended motion with controlled breathing. The waveform section with similar practice of holding breath after maximum inhalation were selected for the DTW analysis. The algorithm first determined the segmentation by identifying peaks and peak-to-peak intervals. Then, the average interval was set as the segment length which was around 703 sampling points under the sampling rate of 1 kSps. The averaged waveforms (FIGS. 14(*a*)-14(*d*)) are set as the templates in DTW. The templates are also shown together with ECG to illustrate the waveform timing in the cardio cycle in FIG. 14(*f*).

Figure 15:
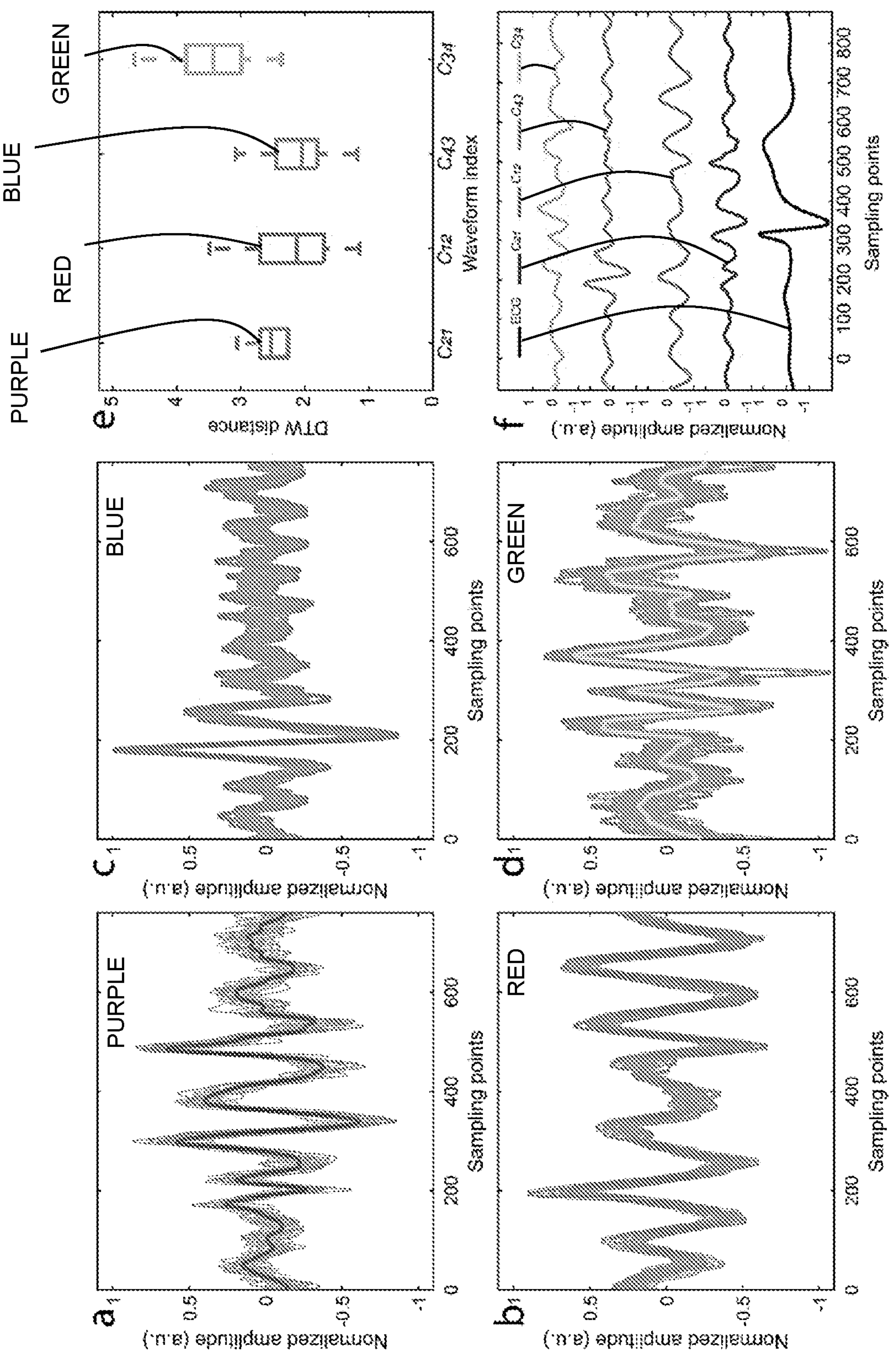
FIG. 15. Graphs showing DTW waveform analyses of 200 heartbeats observed from the same NCS cross-port setup as FIG. 14, on a second person: (a) $C_{21}$; (b) $C_{12}$; (c) $C_{43}$; (d) $C_{34}$. The purple, red, blue and green curves are the averaged waveforms to serve as the template. Other waveforms in the same channel are overlaid as gray curves. (e) The DTW distances against the corresponding template waveforms. (f) The $C_{21}$ to $C_{34}$ waveform templates in comparison with ECG.

In FIG. 15, a second user was tested under the same NCS cross-port setup described in FIG. 14. The averaged segment length was 760 sampling points under the same sampling rate of 1 kSps. The timing features with significant signal strength in the templates were similar between the two users. Variation of waveforms in FIGS. 14 and 15 could be caused by the placement of the sensing antenna and the physiological differences between individuals.

FIG. 16 shows the correlation of the cross-port channels by the DTW distance among various group comparisons. In Group 1, the left-most bar is the medium $C_{21}$ DTW distance of the first person shown in FIG. 14(*e*), and the middle bar is the medium $C_{21}$ DTW distance of the second person shown in FIG. 15(*e*). The right-most bar is the DTW distance between the $C_{21}$ template waveforms of the first and the second persons. Groups 2-4 are the similar analyses of $C_{12}$, $C_{43}$ and $C_{34}$, respectively. In Group 5, the left-most bar is the DTW distance calculated between the $C_{21}$ and $C_{12}$ templates of the first person, and the second bar (from left) is the one from the second person. The third bar is the DTW distance between the $C_{21}$ template of the first person and the $C_{12}$ template of the second person, and the fourth bar is between the $C_{12}$ template of the first person and $C_{21}$ template of the second person. Groups 6-10 are the similar analyses of $C_{21}$ to $C_{43}$, $C_{21}$ to $C_{34}$, $C_{12}$ to $C_{43}$, $C_{12}$ to $C_{34}$ and $C_{43}$ to $C_{34}$, respectively. From these results we can see that the DTW distances calculated from different channels and different persons are much higher (Group 5 to 10) than the distances from the same person and the same channel. The large DTW distances from the different channels indicates the independent information in each cross-port channel, while the mid-sized DTW distances from different persons of the same cross-port channel can result from antenna placement and physiological variations.

FIG. 18(*a*) shows the electronic hardware schematic in the test embodiment. The NCS antennas are attached on the user's clothing, and the ECG electrodes and the digital stethoscope (ST) are pasted on the user's bare skin. The stethoscope is connected to the audio card of the computer. The ECG electrodes are connected to the ECG recorder, and the digitized signal is transferred to the computer through a USB cable. Four NCS antenna pairs are connected to the two SDRs of MIMO NCS as shown in FIG. 4(*a*). The SDRs are synchronized and the digitized signal is transferred to the computer also through a USB cable. The stethoscope and ECG subsystems are optional, which are just for the waveform comparison of the NCS signal. FIG. 18(*b*) shows the software function blocks and data flow. Data from the stethoscope data, ECG and NCS are first processed in LabVIEW at the data synchronizer (DS). Then the ST and ECG data are fed to the display function directly. The NCS data go to the demultiplexer (DEMUR) to sort out the NCS channels (16 channels in full 4x4 MIMO). Each channel signal will go through the digital down-converter (DDC) to formulate the raw NCS signal. After proper filtering, the NCS signals with different emphases are shown on the screen. The Lab VIEW software also provides the configuration functions for stethoscope, ECG and SDR to control the unit operations. The raw NCS data are also fed to the MATLAB algorithms where waveform analyses and HHT are performed.

Seat Integration

Figure 27:
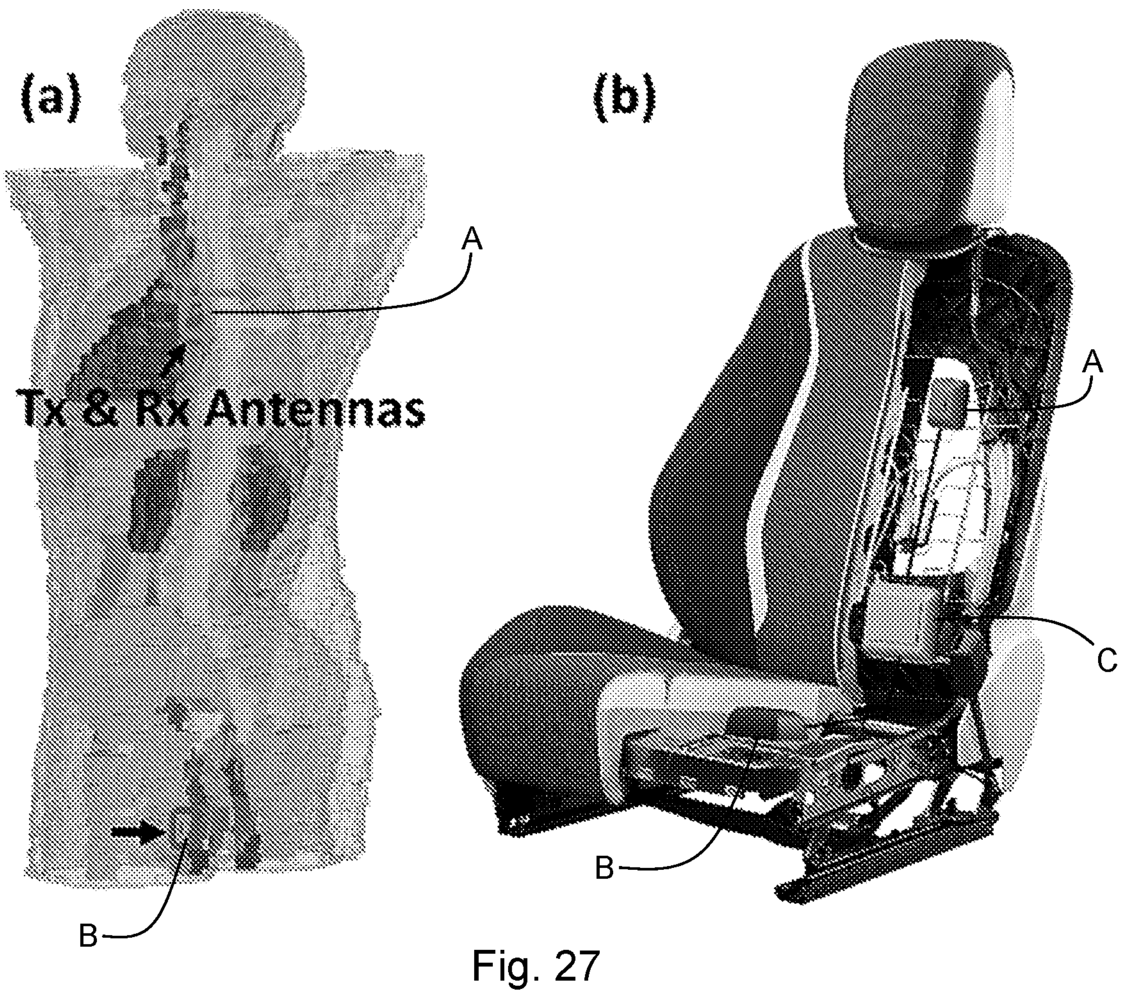
FIG. 27. Vital-sign monitoring by active near-field coherent sensing. (a) Deployment of the sensing antennas close to the heart from the back and the thigh artery from the bottom. (b) An illustration showing an embodiment of the present disclosure with a sensor integrated in a seat—seat back and cushion.

The system can be integrated into a cushion or mat or the like and hence be "invisible" to a user or, at the very least, unobtrusive. The system includes sensing antennas that may be positioned to be close to the mechanical motion sources of targeted vital signs. For example, FIG. 27(*b*) shows a possible schematic for an exemplary NCS system integrated into seat and back cushions. FIG. 27(*b*) shows a first sensing module in the box labeled 'A' having an antenna positioned at the lower part of the left rhomboid major area in the electromagnetic torso model (FIG. 27(*a*)-back 45° view) for heart sensing. Another sensing module in the box labeled 'B' has an antenna positioned close to the upper thigh area to target the femoral pulse. The modules may be connected to a console (labeled 'C') which provides power, synchronization, and/or signal processing. Such a seat-integrated NCS system can be configured to sense, for example, heartbeat, respiration, and/or pulse, as well as parameters such as pulse transit time, to estimate the blood pressure.

The present disclosure may be embodied as a method for non-contact measurement of a body motion of an individual (e.g., on-body or inside-body motion). The individual may be, for example, a human or a non-human animal. The detected motion may be, for example, a heart motion, a pulse, a respiration motion, a bowel motion, an eye motion, or other body motion as will be apparent in light of the present disclosure. A first radiofrequency ("RF") sensing signal is provided within a near-field coupling range of a first motion to be measured to generate a measurement signal. The first sensing signal will be modulated by the first motion thereby generating a first measurement signal. The method includes detecting the first measurement signal. For example, using a near-field Rx antenna to detect a reflected signal. With an antenna within the near-field coupling range of the mechanical motion inside the body, the reflected wave can be readily detected in a coherent manner and will contain information of the mechanical motion.

The first sensing signal is matched to the first measurement signal using a cancellation network as further described below. The cancellation network is used to reduce any non-modulated first sensing signal that is detected along with the first measurement signal. The first motion is measured based on the first measurement signal with reduced non-modulated first sensing signal. In some embodiments, feedback information is obtained from the first measurement signal through timing and magnitude. The first sensing signal is matched with the first measurement signal based on the feedback information to obtain a combined signal. The combined signal is demodulated to obtain the first motion signal. Measuring the first motion may further comprise filtering the first measurement signal using a first frequency range corresponding to the first motion. In some embodiments, a second motion is measured by, for example, filtering the first measurement signal using a second frequency range corresponding to the second motion.

In another aspect, the present disclosure may be embodied as a system for measuring motion of an individual. The system includes a first signal source for generating a first sensing signal. A first Tx antenna is in electrical communication with the first signal source. The first Tx antenna is configured to be disposed within a near-field coupling range of a first motion to be measured. For example, the first Tx antenna may be configured to be disposed within a coupling range of a heart motion, a pulse, a respiration motion, a bowel motion, an eye motion, etc. In this way, a first measurement signal is generated by the first sensing signal modulated by the first motion.

The system includes a first Rx antenna for detecting the first measurement signal (the first sensing signal coupled with (modulated by) the first motion). The first Rx antenna may be configured to receive the first measurement signal as reflected by the body of the individual. A signal processing circuit is configured to match the first sensing signal and the first measurement signal as further described herein. The signal processing circuit may be, for example, a cancellation network. The cancellation network may be configured to reduce in-band self-jamming interferences. In some embodiments, the cancellation network may include a coupler configured to receive the first sensing signal from the first signal source; an attenuator configured to attenuate the amplitude of the first sensing signal based on feedback information; a phase shifter configured to shift the phase of the first sensing signal based on the feedback information; a frequency doubler configured to double a frequency of the first sensing signal; and a combiner configured to match the modified first sensing signal with the first measurement signal. The system may include a bandpass filter configured to filter the first measurement signal using a first frequency range corresponding to the first motion.

In some embodiments, the system may be configured to measure a second motion. For example, the system may include a second signal source for generating a second sensing signal and a second Tx antenna configured to be disposed within a near-field coupling range of the second motion. In this way, the second sensing signal may be modulated by the second motion to generate a second measurement signal. A second Rx antenna is provided to receive the second measurement signal.

The signal processing circuit may be, for example, a processor (such as a digital-signal processor ("DSP")) programmed to sample, demodulate, and/or filter the first measurement signal to derive the motion signal.

Seat-Integrated System Design and Experimental Results

As shown in FIG. 27(*a*), when the antenna transmits the sensing signal, a significant part of the RF energy will couple into the human body (the dotted-line arrow pointing left) in the near-field region, where the motion of the dielectric boundaries will change both the radiation into the free space and the reflection back to the transmitter (Tx). For the seat setup, use of far-field sensing is inconvenient as an external reader, off of the chair, is required. The noisy RF ambient environment in vehicle cabins may also create challenges. The present device utilizes NCS antenna reflection, although implementation of this technology includes its own set of challenges. NCS signals from the back and thigh of an individual are weaker than those from the chest and wrist because the heart and femoral artery are positioned deeper in the body with respect to the antenna. When a commercial antenna designed for operation in free-space is deployed for the human body, the antenna will be detuned, resulting in a large antenna reflection to the receiver (Rx) low-noise amplifier (LNA). The weak NCS signal can be easily saturated out due to the limited precision of analog-to-digital converters (ADC) in processing the baseband. Furthermore, circulator with high Tx-to-Rx isolation are often bulky, and not using such a circulator may result in further Rx saturation by self-interference causing loss of the NCS signal.

To reduce the overall system size and enable fast software-defined radio (SDR) prototyping, a self-contained NC S system with a pair of small commercial antennas was designed in which the motion of the dielectric boundary inside the body will modify the near-field coupling between the two antennas. The non-modulated coupling of the Tx-to-Rx signal in FIG. 1 including a signal at frequency f and a signal at frequency 2*f* in all possible paths will is adaptively reduced by the cancellation network to enhance the NCS sensitivity. The Rx antenna can be deployed closed to the Tx antenna for a small system size, as long as a significant portion of the RF energy from the Tx antenna will be in the region of interest inside the body of the individual. The non-modulated signals should not saturate Rx due to LNA linearity and ADC dynamic range so that their magnitude and phase can be reasonably measured. The Rx signal model here may be thought of as similar to the principle of operation of an interferometer. As the amplitudes of the modulated and the non-modulated reference signals approach the same level, the system can achieve the improved modulation efficiency and dynamic range in the demodulated signal magnitude after the Rx gain.

FIG. 1 shows a block diagram of an exemplary experimental system was constructed using an SDR (Ettus X310) configured as a 2nd harmonic transceiver, so as to reduce self-interference and to improve the NCS signal-to-noise ratio (SNR). Tx and Rx frequency synthesizers share the same clock source, so the transceiver is coherent and can demodulate both the amplitude and phase information of the Rx signal. In the experimental embodiment, the Tx signal was transmitted from the Tx port at a frequency f around 475 MHz. A major part of the RF energy was transmitted through the coupler (CPL) to a frequency doubler (FD) and then to a Tx antenna where the sensing signal is coupled to the human body at the harmonic frequency in the 950 MHz band. The signal chain from CPL to the combiner (CB) is a cancellation network which is configured to, for example, match the received modulated and non-modulated signals to achieve improved modulation efficiency and dynamic range. The coupled signal from CPL goes through a tunable attenuator (ATT) and a tunable phase shifter (PS) and is then converted to the 2nd harmonic signal by a frequency doubler (FD). The balancing signal is then combined with the received NC S-modulated signal from the Rx antenna, feeding into the Rx port of the SDR. Based on the received signal, ATT and PS can be feedback-controlled to improve signal quality. In the experimental embodiment. the digital signals were processed a computer using LabVIEW. The equivalent sampling rate of the vital signs was 500 samples per second (Sps).

Figure 28:
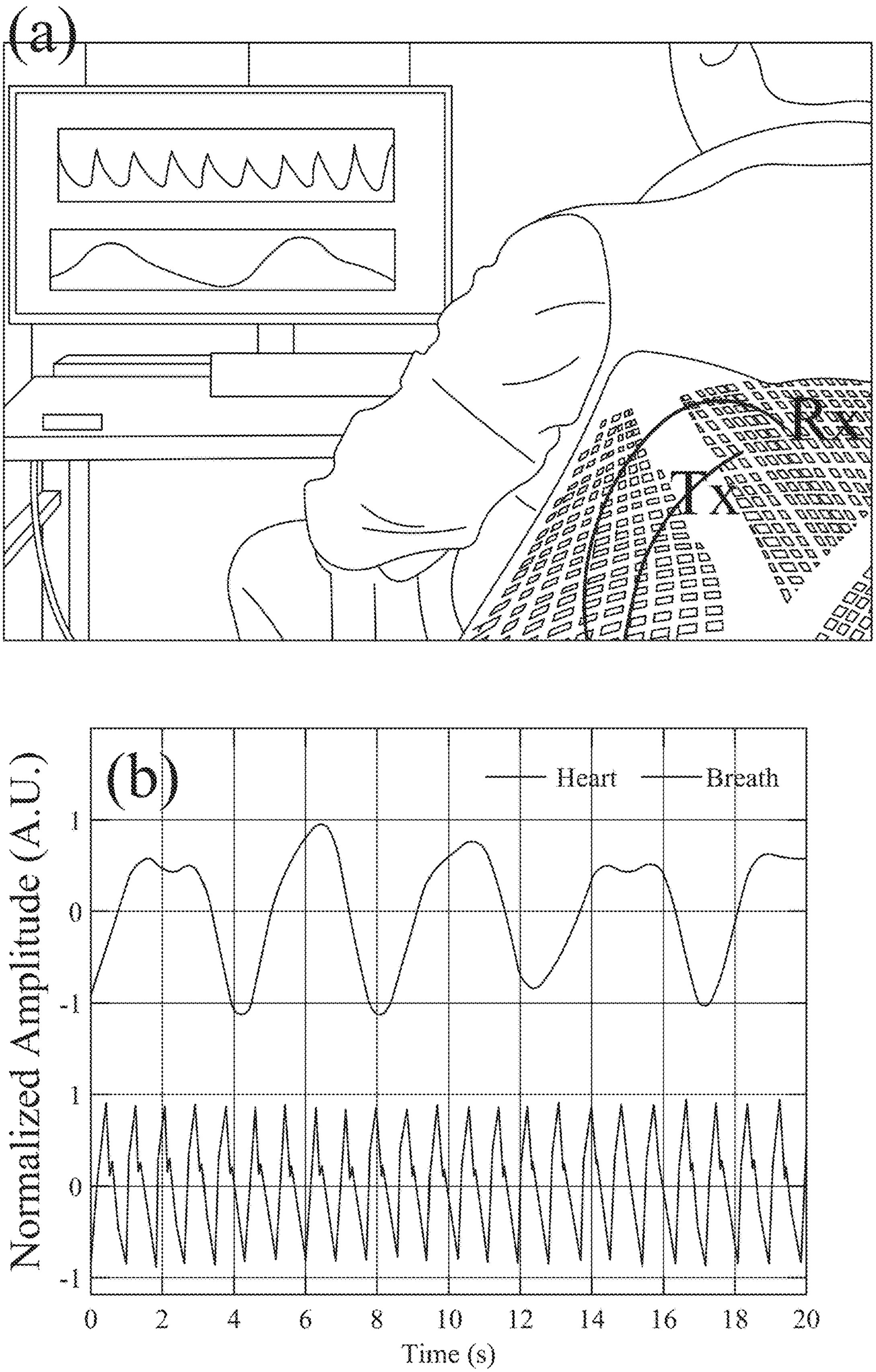
FIG. 28. Experimental setup on a seated user with NCS measurements. (a) Photo with the visible sensing antenna mounted on the outside back of the chair. (b) Measured respiration (top trace) and heartbeat (bottom trace).
Figure 29:
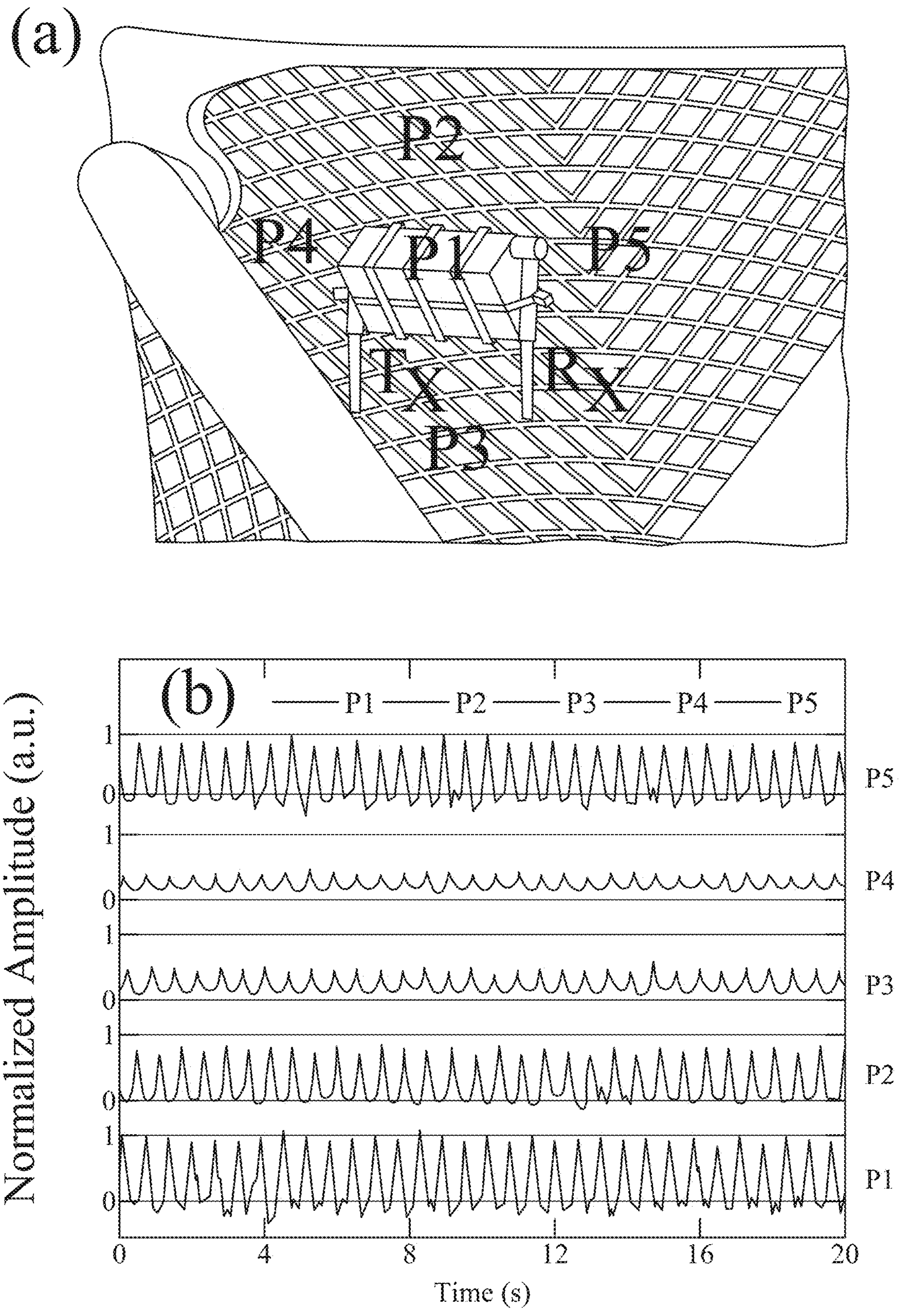
FIG. 29. Experiments with different sensing antenna positions. (a) Sensing antennas in five locations. (b) The heartbeat signals from each position of (a).

The sensed of heartbeat and respiration from the seatback Tx-Rx antennas of the experimental embodiment is shown in FIG. 28(*a*). A user is seated in a chair in which Tx and Rx antennas are mounted. The computer screen shows the heartbeat (top) and the respiration (bottom) waveforms. As can be seen in FIG. 28(*a*), there is no need for direct skin contact—the person under test can wear typical clothes. In FIG. 28(*b*), the top curve shows the respiration waveform after a bandpass filter from 0.1 Hz to 0.9 Hz was applied. The bottom curve shows the cardio waveform after a bandpass filter from 0.8 Hz to 50 Hz was applied. Because the NCS signal measures the mechanical motion, the NCS heartbeat signal mostly reflects the fundamental beating of the heart. In some embodiments, the cancellation network may be configured to compensate for interference produced by body motion. The experimental embodiment was also used to investigated antenna placement variation for the heartbeat signal to estimate effects resulting from variations in posture and body size. The antenna pair was mounted at the five positions (P1 to P5) shown in FIG. 29(*a*), and corresponding extracted heartbeat waveforms are shown in FIG. 29(*b*). System settings were controlled to give the same measurement configurations, and the waveforms were normalized to the maximum amplitude of the signal from P1. When the sensing antenna pair was at P1, P2, and P5, the signal strengths were at similar levels. At P3 and P4, the increased offset to the heart position made the signal much weaker with reduced SNR.

A second parallel SDR system was employed to detect the femoral pulse at a corresponding position (e.g., in the seat bottom). In the experimental Ettus X310 SDR system, dual RF daughter boards (UBX 160-MHz) were used, and the daughter boards were RF and baseband synchronized. Other SDR platforms, such as but not limited to Ettus B210, are also capable of providing two pairs of transceivers. In some embodiments, the synchronized baseband can enable the reader CDMA protocol such that multiple readers can share the same reading zone with minimal interference.

Figure 30:
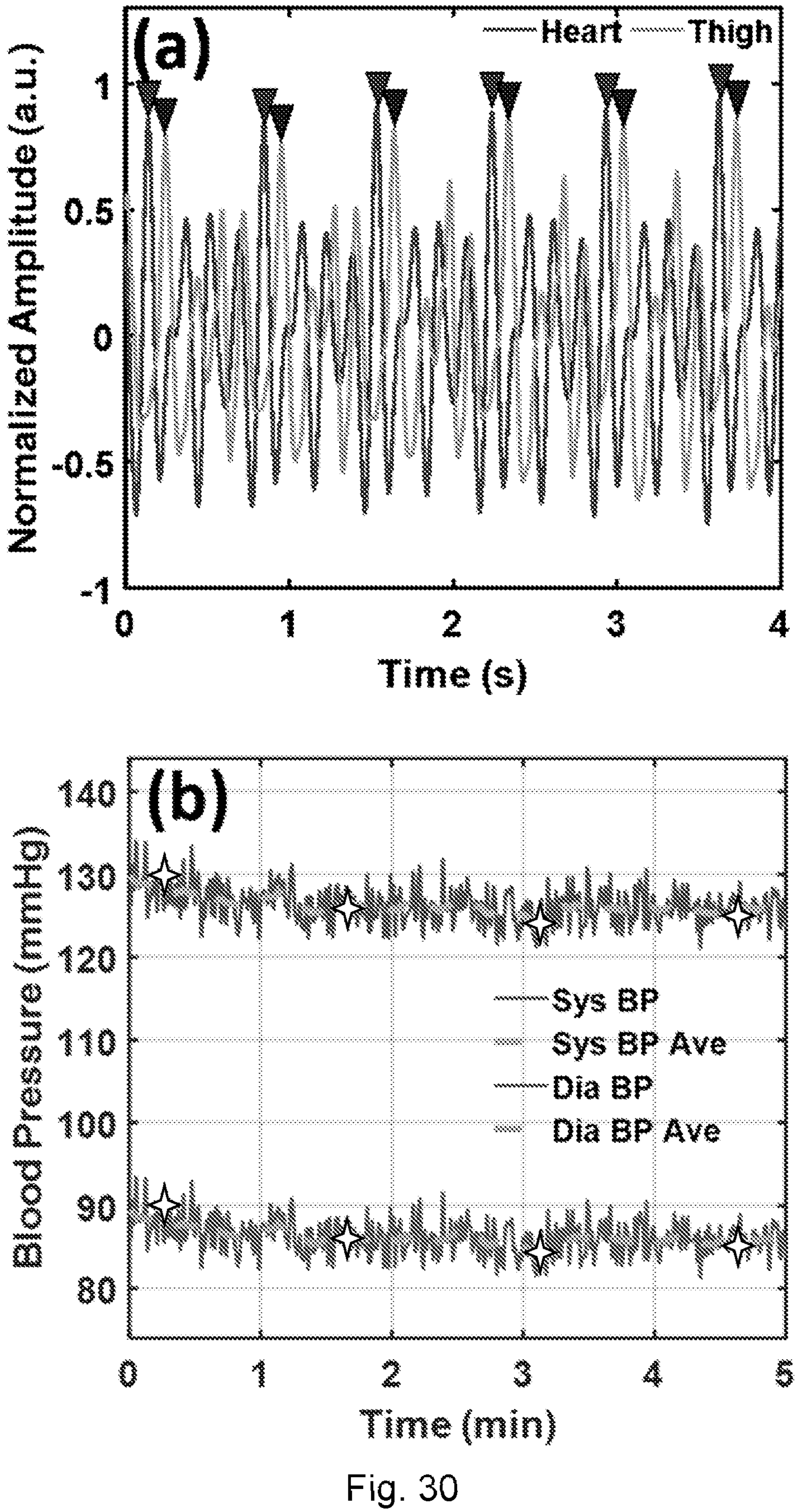
FIG. 30. PTT-based blood pressure estimates. (a) Graph showing synchronized heartbeat and femoral pulse signals after the equalization. The markers indicate the peak for PTT calculation. (b) Graph showing calibrated PTT based blood pressure. The white star markers are the results from a cuff-based commercial blood pressure monitor.

Measurement of the femoral pulse can be used for multiple purposes, either as an independent signal or in combination with one or more signals. For example, the femoral pulse may be used (a) to provide an estimate of the heartrate even when the seat occupant is out of position (e.g., not seated against the seatback) and the signal from the seat back is lost; and (b) in combination with the heart signal to derive a pulse transit time (PTT) from the heart to the peripheral artery so as to estimate the blood pressure. Because the NCS signal is dominated by the fundamental motion component in comparison with its harmonics, to achieve higher PTT accuracy, the signals may be equalized to amplify the high-frequency components to pick out the sharp peaks. As shown in FIG. 30(*a*), the sharp peaks of the equalized heartbeat (black) and femoral pulse (gray) waveforms were detected to calculate PTT. After calibration, the derived systolic (top) and diastolic (bottom) blood pressures are shown in FIG. 30(*b*), where the dash curves represented their moving averages for every twelve heartbeats. The markers show blood pressure results measured using an arm-cuff blood pressure monitor (OMRON BP760N), where the arm remained steady at the heart level. At the beginning, both systolic and diastolic pressures were slightly high around 131 mmHg and 90 mmHg, because the occupant under test just took the seat. The pressures dropped to 125 mmHg and 85 mmHg after quiet sitting. Compared to the cuff-based method, the current PTT method can estimate blood pressure at each heartbeat without the need for additional devices, which may be cumbersome and uncomfortable.

Although the present disclosure has been described with respect to one or more particular embodiments, it will be understood that other embodiments of the present disclosure may be made without departing from the spirit and scope of the present disclosure.

What is claimed is:

1. A system for measuring motion of an individual, comprising:

a first signal source for generating a first sensing signal;

a first Tx antenna in electrical communication with the first signal source and wherein the first Tx antenna is configured to be disposed within a near-field coupling range of a first motion to be measured such that the first sensing signal is modulated by the first motion to generate a first measurement signal;

a first receiver for detecting the first measurement signal;

a first Rx antenna in communication with the first receiver; and a signal processing circuit configured to match the first sensing signal and the first measurement signal, the signal processing circuit comprising a cancellation circuit, wherein the first sensing signal and the first measurement signal are matched using the cancellation circuit to reduce one or more non-modulated first sensing signals that are detected in addition to the first measurement signal, and wherein the first motion is measured based on the first measurement signal with the reduced one or more non-modulated first sensing signals, wherein the cancellation circuit comprises a coupler configured to receive the first sensing signal from the first signal source, an attenuator configured to attenuate an amplitude of the first sensing signal based on feedback information, a phase shifter configured to shift a phase of the first sensing signal based on the feedback information, a frequency doubler configured to double a frequency of the first sensing signal, and a combiner configured to match the attenuated first sensing signal with the first measurement signal.

2. The system of claim 1, further comprising a bandpass filter configured to filter the first measurement signal using a first frequency range corresponding to the first motion.

3. The system of claim 1, wherein the first Tx antenna is configured to be disposed within a coupling range of a heart motion, a pulse, and/or a respiration motion.

4. The system of claim 1, wherein the first Tx antenna and the first Rx antenna are disposed within a seat.

5. The system of claim 1, further comprising:

a second signal source for generating a second sensing signal;

a second Tx antenna in electrical communication with the second signal source and wherein the second Tx antenna is configured to be disposed within a near-field coupling range of a second motion to be measured such that the second sensing signal is modulated by the second motion to generate a second measurement signal;

a second receiver configured to detect the second measurement signal;

a second Rx antenna in electrical communication with the second receiver; and wherein the signal processing circuit is configured to match the second sensing signal and the second measurement signal.

6. The system of claim 5, wherein the first receiver is configured to detect a cross-coupled measurement signal based on the second sensing signal.

7. The system of claim 5, further comprising:

a third signal source for generating a third sensing signal;

a third Tx antenna in electrical communication with the third signal source and wherein the third Tx antenna is configured to be disposed within a near-field coupling range of a third motion to be measured to provide a third sensing signal to be modulated by the third motion to generate a third measurement signal;

a third Rx antenna for receiving the third measurement signal; a fourth signal source for generating a fourth sensing signal;

a fourth Tx antenna in electrical communication with the fourth signal source and wherein the fourth Tx antenna is configured to be disposed within a near-field coupling range of a fourth motion to be measured to provide a fourth sensing signal to be modulated by the fourth motion to generate a fourth measurement signal; and a fourth Rx antenna for receiving the fourth measurement signal.

8. The system of claim 7, wherein the first receiver is configured to detect a cross-coupled measurement signal based on the third sensing signal and/or the first receiver is configured to detect a cross-coupled measurement signal based on the fourth sensing signal.

9. The system of claim 7, wherein the second receiver is configured to detect one or more cross-coupled measurement signals based on a corresponding one or more of the first sensing signal, the third sensing signal, and the fourth sensing signal.

10. The system of claim 1, further comprising a processor configured to confirm an identity of the individual.

11. The system of claim 10, wherein the processor is configured to confirm the identity of the individual based on a dynamic time warping (DTW) distance of a cross-coupled measurement signal.

12. The system of claim 1, further comprising a first downlink source for generating a downlink signal, and wherein the first signal source is a wireless tag configured to receive the downlink signal and generate the first sensing signal.

13. A system for measuring motion of an individual, comprising:

a first signal source for generating a first sensing signal;

a first Tx antenna in electrical communication with the first signal source and wherein the first Tx antenna is configured to be disposed within a near-field coupling range of a first motion to be measured such that the first sensing signal is modulated by the first motion to generate a first measurement signal;

a first receiver for detecting the first measurement signal;

a first Rx antenna in communication with the first receiver;

a signal processing circuit configured to match the first sensing signal and the first measurement signal, the signal processing circuit comprising a cancellation circuit, wherein the first sensing signal and the first measurement signal are matched using the cancellation circuit to reduce one or more non-modulated first sensing signals that are detected in addition to the first measurement signal, and wherein the first motion is measured based on the first measurement signal with the reduced one or more non-modulated first sensing signals;

a second signal source for generating a second sensing signal;

a second Tx antenna in electrical communication with the second signal source and wherein the second Tx antenna is configured to be disposed within a near-field coupling range of a second motion to be measured such that the second sensing signal is modulated by the second motion to generate a second measurement signal;

a second receiver configured to detect the second measurement signal;

a second Rx antenna in electrical communication with the second receiver, wherein the signal processing circuit is configured to match the second sensing signal and the second measurement signal; and a processor configured to confirm an identity of the individual based on a dynamic time warping (DTW) distance of a cross-coupled measurement signal.

14. The system of claim 13, wherein the first receiver is configured to detect a cross-coupled measurement signal based on the second sensing signal.

15. The system of claim 13, further comprising:

a third signal source for generating a third sensing signal;

a third Tx antenna in electrical communication with the third signal source and wherein the third Tx antenna is configured to be disposed within a near-field coupling range of a third motion to be measured to provide a third sensing signal to be modulated by the third motion to generate a third measurement signal;

a third Rx antenna for receiving the third measurement signal; a fourth signal source for generating a fourth sensing signal;

a fourth Tx antenna in electrical communication with the fourth signal source and wherein the fourth Tx antenna is configured to be disposed within a near-field coupling range of a fourth motion to be measured to provide a fourth sensing signal to be modulated by the fourth motion to generate a fourth measurement signal; and a fourth Rx antenna for receiving the fourth measurement signal.

16. The system of claim 13, further comprising a first downlink source for generating a downlink signal, and wherein the first signal source is a wireless tag configured to receive the downlink signal and generate the first sensing signal.

17. A system for measuring motion of an individual, comprising:

a first signal source for generating a first sensing signal;

a first Tx antenna in electrical communication with the first signal source and wherein the first Tx antenna is configured to be disposed within a near-field coupling range of a first motion to be measured such that the first sensing signal is modulated by the first motion to generate a first measurement signal;

a first receiver for detecting the first measurement signal;

a first Rx antenna in communication with the first receiver;

a signal processing circuit configured to match the first sensing signal and the first measurement signal, the signal processing circuit comprising a cancellation circuit, wherein the first sensing signal and the first measurement signal are matched using the cancellation circuit to reduce one or more non-modulated first sensing signals that are detected in addition to the first measurement signal, and wherein the first motion is measured based on the first measurement signal with the reduced one or more non-modulated first sensing signals; and a first downlink source for generating a downlink signal, and wherein the first signal source is a wireless tag configured to receive the downlink signal and generate the first sensing signal.

18. The system of claim 17, wherein the wireless tag further comprises an energy-harvesting circuit, and wherein the energy-harvesting circuit is configured to power the wireless tag using the downlink signal.

19. The system of claim 17, wherein the first sensing signal has a frequency which is a harmonic of a frequency of the downlink signal.

20. The system of claim 17, further comprising a processor configured to determine a blood pressure based on the first measurement signal.

* * * * *